(12) United States Patent
Madio et al.

(10) Patent No.: US 6,841,996 B2
(45) Date of Patent: Jan. 11, 2005

(54) NUCLEAR MAGNETIC RESONANCE APPARATUS AND METHODS FOR ANALYZING FLUIDS EXTRACTED FROM EARTH FORMATION

(75) Inventors: David P. Madio, Danbury, CT (US); Robert L. Kleinberg, Ridgefield, CT (US); Richard W. Gaylor, Brookfield, CT (US); Robert Freedman, Houston, TX (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/349,011

(22) Filed: Jan. 22, 2003

(65) Prior Publication Data

US 2004/0140800 A1 Jul. 22, 2004

(51) Int. Cl.⁷ .................................................. G01V 3/00
(52) U.S. Cl. ...................................... 324/303; 324/306
(58) Field of Search ................................. 324/303, 306, 324/307, 309, 318, 322

(56) References Cited

U.S. PATENT DOCUMENTS

| | | |
|---|---|---|
| 2,912,641 A | 11/1959 | Ruble |
| 3,597,681 A | 8/1971 | Huckabay et al. ....... 324/0.5 R |
| 4,291,271 A | 9/1981 | Lauffer ....................... 324/307 |
| 4,629,986 A | 12/1986 | Clow et al. .................. 324/303 |
| 4,860,581 A | 8/1989 | Zimmerman et al. ......... 73/155 |
| 4,936,139 A | 6/1990 | Zimmerman et al. ......... 73/155 |
| 4,994,777 A | 2/1991 | Leupold et al. ............. 335/302 |
| 5,023,551 A | 6/1991 | Kleinberg et al. .......... 324/303 |
| 5,055,787 A | 10/1991 | Kleinberg et al. .......... 324/303 |
| 5,306,640 A | 4/1994 | Vinegar et al. ............... 436/29 |
| 5,428,291 A | 6/1995 | Thomann et al. ........... 324/303 |
| 5,680,043 A | 10/1997 | Hurlimann et al. ......... 324/303 |
| 5,705,927 A | 1/1998 | Sezginer et al. ............ 324/303 |
| 5,796,252 A | 8/1998 | Kleinberg et al. .......... 324/303 |
| 5,939,717 A | 8/1999 | Mullins ...................... 250/255 |
| 6,107,796 A | 8/2000 | Prammer .................... 324/303 |
| 6,111,408 A | 8/2000 | Blades ........................ 324/303 |
| 6,111,409 A | 8/2000 | Edwards et al. ............ 324/303 |
| 6,274,865 B1 | 8/2001 | Schroer et al. .......... 250/269.1 |
| 6,346,813 B1 | 2/2002 | Kleinberg ................... 324/303 |
| 6,350,986 B1 | 2/2002 | Mullins et al. .......... 250/269.1 |

(List continued on next page.)

FOREIGN PATENT DOCUMENTS

| | | | |
|---|---|---|---|
| GB | 2 291 198 A | 7/1994 | ........... G01F/1/596 |
| WO | WO 98/59220 | 6/1998 | |

OTHER PUBLICATIONS

Amyx, J. W. et al. "Petroleum Reservoir Engineering". *McGraw–Hill* (1960), p. 458.

Andrew, E. R. "Nuclear Magnetic Resonance". *Cambridge University Press* (1955), p. 127.

Badry, R. et al. "Downhole Optical Analysis of Formation Fluids". *Oilfield Review* (Jan. 1994), pp. 21–28.

(List continued on next page.)

*Primary Examiner*—Louis Arana
(74) *Attorney, Agent, or Firm*—Jody Lynn DeStefanis; William B. Batzer; John J. Ryberg

(57) ABSTRACT

The present invention discloses a method and apparatus to make a nuclear magnetic resonance measurement on a flowing fluid using varied wait times. In one method, NMR measurements are made by: a) flowing the fluid through a static magnetic field; b) applying a group of oscillating magnetic field pulses to the flowing fluid, wherein the group of pulses is comprised of an initial pulse and one or more refocusing pulses; c) detecting magnetic resonance signals from the flowing fluid; d) after a wait time, repeating (b) and (c) one or more times, wherein at least two of the repetitions have varied wait times; and e) analyzing the detected magnetic resonance signals to extract information about the flowing fluid. Further, varied wait time measurements may be useful in determining the flow rate of the sample.

28 Claims, 24 Drawing Sheets

U.S. PATENT DOCUMENTS

| | | | | |
|---|---|---|---|---|
| 6,366,087 B1 | * | 4/2002 | Coates et al. | 324/303 |
| 6,439,046 B1 | | 8/2002 | Kruspe et al. | 73/152.01 |
| 6,492,809 B1 | | 12/2002 | Speier et al. | 324/303 |
| 6,661,226 B1 | * | 12/2003 | Hou et al. | 324/303 |
| 2002/0075000 A1 | | 6/2002 | Pammer et al. | 324/315 |
| 2003/0006768 A1 | | 1/2003 | Kleinberg et al. | 324/303 |

OTHER PUBLICATIONS

Bloembergen et al. "Relaxation Effects in Nuclear Magnetic Resonance Absorption". *Physical Review* (1948), vol. 73, No. 7, pp. 679–712.

Botto, R. E. "Fossil Fuels". *Encyclopedia of Nuclear Magnetic Resonance* (1996), pp. 1–17.

CRC Handbook of Chemistry and Physics (63rd Edition). *CRC Press* (1982–1983), pp. B–73–B–165.

Callaghan, P. T. "Principles of Nuclear Magnetic Resonance Microscopy". *Clarendon Press* (1991).

Caprihan, A. et al. "Flow Measurements by NMR". *Physics Reports* 198 (1990), pp. 195–235.

Collins, A. G. "Properties of Produced Waters". *Petroleum Engineering Handbook,* Chapter 24, pp. 24–1–24–23.

Dechter, J. J. "Progress in Inorganic Chemistry", vol. 29 (1982), pp. 314–385.

Dyer, J. R. "Applications of Absorption Spectroscopy of Organic Compounds". *Prentice–Hall* (1965), pp. 84–85.

Farrar, T. C. et al. "Pulse and Fourier Transform NMR". *Academic Press* (1971).

Freedman, R. et al. "A New NMR Method of Fluid Characterization in Resrvoir Rocks: Experimental Confirmation and Simulation Results". *SPE 63214,* Annual Technical Conference and Exhibition (Oct. 2000), pp. 1–15.

Fukushima, E. et al. "Experimental Pulse NMR. A Nuts and Bolts Approach". *Addison–Wesley* (1981).

Gerstein et al. "Transient Techniques in NMR of Solids". *Academic Press* (1985), pp. 240–248.

Halbach, K. "Design of Permanent Multipole Magnets with Oriented Rare Earth Cobalt Material", *Nuclear Instruments and Methods* 169 (1980), pp. 1–10.

Halbach, K. "Physical and Optical Properties of Rare Earth Cobalt Magnets". *Nuclear Instruments and Methods* 187 (1981), pp. 109–117.

Horkowitz, J. P. et al. "Residual Oil Saturation Measurements in Carbonates with Pulsed NMR Logs". *SPWLA 36th Annual Logging Symposium* (Jun. 1995), Paper Q, pp. 1–12.

Hurlimann, M. D. et al. "Spin Dynamics of Carr–Purcell–Melboom–Gill–like Sequences in Grossly Inhomogeneous $B_0$ and $B_1$ Fields and Application to NMR Well Logging". *Journal Magn. Reson.,* vol. 143 (2000), pp. 120–135.

Hurlimann, M. D. "Optimization of Timing in the Carr–Purcell–Meiboom–Gill Sequence". *Magn. Reson. Imaging,* vol. 19 (2001), pp. 375–378.

Kleinberg, R. L. "Well Logging". *Encyclopedia of Nuclear Magnetic Resonance,* vol. 8 (1996), pp. 4960–4969.

Kleinberg, R. L. et al. "NMR Properties of Reservoir Fluids". *Log Analyst,* (Nov. –Dec. 1996), pp. 20–32.

Kleinberg, R. L. et al. "Review: NMR Detection and Characterization of Hydrocarbons in Subsurface Earth Formations". *Spatially Resolved Magnetic Resonance* (1998), pp. 556–573.

Li, J. C. M. et al. "Self–Diffusion Coefficient and Viscosity in Liquids". *J. Chem. Phys.,* vol. 23, No. 3 (Mar. 1955), pp. 518–520.

Laszlo, Pierre. "Quadrupolar Nuclei in Liquid Samples". *Encyclopedia of Nuclear Magnetic Resonance* (1996), pp. 3858–3868.

Morriss, C. E. et al. "Hydrocarbon Saturation and Viscosity Estimation from NMR Logging in the Belridge Diatomite". *Log Analyst* (Mar.–Apr. 1997), p. 44–59.

Petrakis, L. et al. "The Utilization of Nuclear Magnetic Resonance Spectroscopy for Petroleum, Coal, Oil Shale, Petrochemicals, and Polymers. Phenomenology, Paradigms of Applications, and Instrumentation". *Applied Spectroscopy Reviews,* vol. 15(2) (1972), pp. 195–260.

Rummens, F. H. A. et al. "Intermolecular Interactions in Nuclear Magnetic Resonance". XI. The $^{13}$C and Proton Medium Shifts of $CH_4$ in the Gas Phase and in Solution. *Canadian Journal of Chemistry* (1977), vol. 55, pp. 3021–3030.

*Schlumberger Wireline & Testing.* "Wireline Formation Testing and Sampling". SMP–7508 (1996), pp. 4–29 and 4–40.

*Schlumberger Wireline & Testing.* "CMR Combinable Magnetic Resonance Tool Client Operating Guide" (Jun. 1996), pp. i–37.

Singer, J. M. et al. "Fast NMR Logging for Bound Fluid and Permeability". *SPWLA 38th Annual Logging Symposium* (Jun. 1997), Paper YY, pp. 1–13.

Straley, C. "An Experimental Investigation of Methane in Rock Materials". *SPWLA 38th Annual Logging Symposium* (Jun. 1997), Paper AA, pp. 1–14.

Tissot, B. P. et al. "Petroleum Formation and Occurrence". *Springer–Verlag* (1978), Fig. IV.1.20.

Trappeniers, N. J. et al. "High Resolution Nuclear Magnetic Resonance Spectroscopy in Liquids and Gases at Pressures up to 2500 Bar". *Physica,* 82A (1976), pp. 581–595.

Vinegar, H. J. et al. "Whole–Core Analysis by $^{13}$C NMR". *SPE Formation Evaluation* 6, (Jun. 1991), pp. 183–189.

Zimmerman, T. "Application of Emerging Wireline Formation Testing Technologies." *OSEA 90105* (1990), pp. 1–7 and pp. 90–95.

* cited by examiner

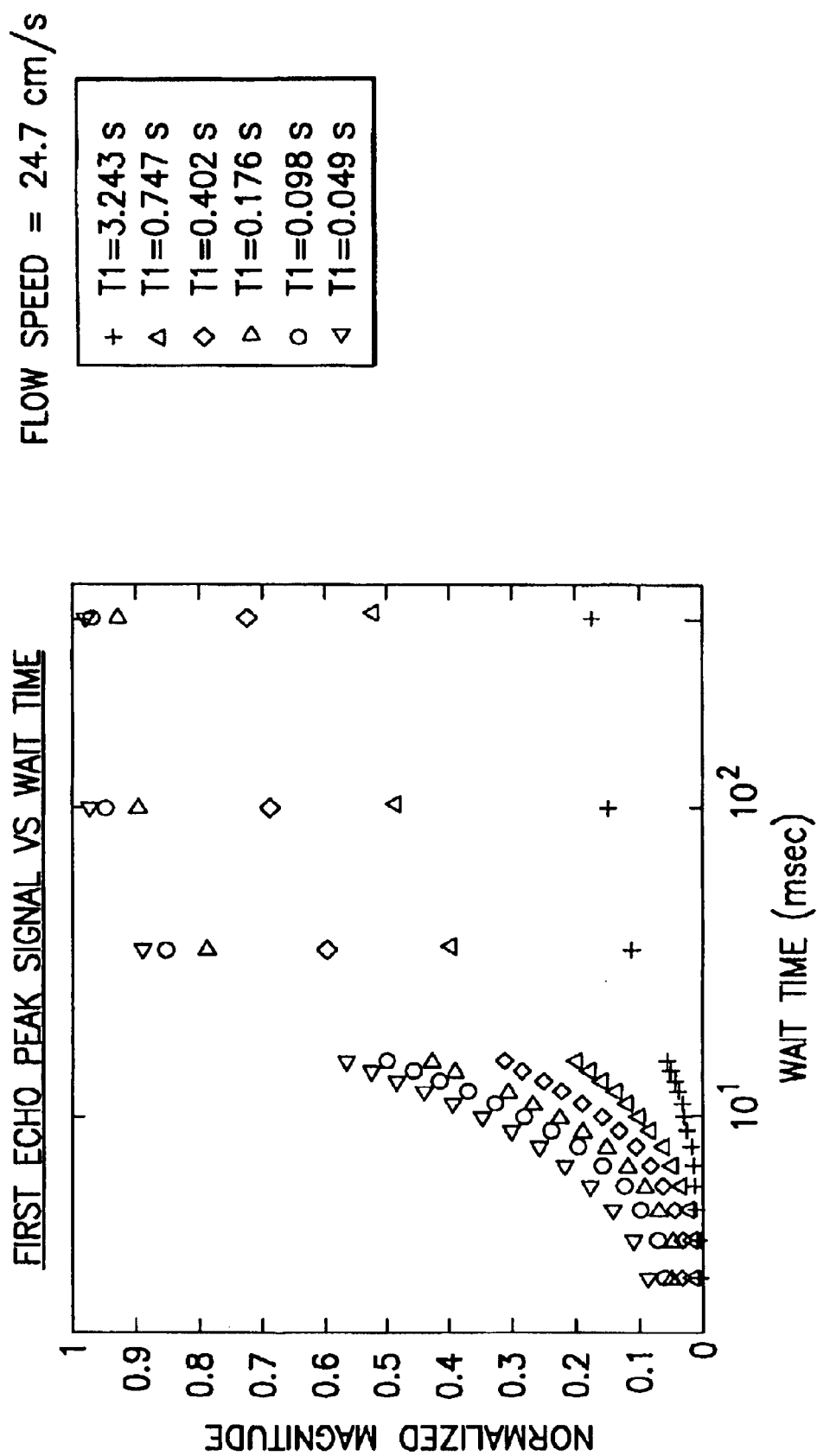

NUCLEAR MAGNETIC RESONANCE APPARATUS AND METHODS FOR ANALYZING FLUIDS EXTRACTED FROM EARTH FORMATION

FIELD OF THE INVENTION

The present invention relates to well logging tools and methods, and more particularly to methods for analyzing extracted formation fluids by magnetic resonance techniques, especially nuclear magnetic resonance (NMR) using variable wait time measurements.

BACKGROUND INFORMATION

Downhole formation fluid sampling tools, such as the Schlumberger Modular Formation Dynamics Tester (MDT™), withdraw samples of fluids from earth formations for subsequent analyses. These analyses are needed to characterize physical properties such as water and oil volume fractions, oil viscosity, and water salinity, among others, and are helpful in contamination monitoring. This knowledge is needed to interpret wireline well logs as well as plan for the efficient exploitation of the reservoir.

Downhole formation fluid sampling tools can withdraw samples of fluids from earth formations and transport them to the surface for analysis. The samples are sent to fluid analysis laboratories for analysis of composition and physical properties. There are many inefficiencies inherent in this process.

Only about six samples can be collected on each descent ("trip") of the tool into the borehole. Because fluid sampling tools are deployed from drilling rigs, and because the rental charge for such rigs can exceed $150,000 per day in the areas where fluid sampling is most often conducted, economic considerations usually preclude multiple trips in the hole. Thus, oil producing formations are almost always undersampled.

Moreover, the samples undergo reversible and irreversible changes as a result of the temperature and/or pressure changes while being brought to the surface and as a result of the transportation process. For example, gases evolve out of solution, waxes precipitate, and asphaltenes chemically recombine. Irreversible changes eliminate the possibility of ever determining actual in situ fluid properties. Reversible changes are deleterious because they occur slowly and therefore impact sample handling and measurement efficiency.

Further, the transportation and handling of fluids uphole entails all the dangers associated with the handling of volatile and flammable fluids at high pressure and temperature. After analyses are complete, the samples must be disposed of in an environmentally acceptable manner, with associated financial and regulatory burdens.

In addition, because fluid analysis laboratories are frequently distant from the well site, there are substantial delays—often several weeks—in obtaining results. If a sample is for some reason corrupted or lost during sampling, transporting, or measurement, there is little possibility of returning to the well to replace it.

No presently deployed system is generally useful for determining the characteristics of sampled formation fluids in-situ while flowing. Accordingly, it is an object of the present invention to provide an apparatus and method which monitors properties while the sample is being taken. It is another object of the present invention to provide an apparatus and method to analyze fluid samples at formation temperature and pressure within the downhole sampling tool.

SUMMARY OF THE INVENTION

The present invention relates to a method and apparatus for performing NMR measurements on a flowing fluid using variable wait times. In accordance with the present invention, the time between groups of pulses is varied, such that at least two different wait times are used. Nearly any variation of wait times is acceptable. For example, wait times may increase, decrease, be a repeating pattern, be random, or be some combination thereof.

In one embodiment, a method of making a nuclear magnetic resonance measurement on a flowing fluid is disclosed comprising: a) flowing the fluid through a static magnetic field; b) applying a group of oscillating magnetic field pulses to the flowing fluid, wherein each group of pulses comprises an initial pulse and one or more refocusing pulses; c) detecting magnetic resonance signals from the flowing fluid; d) after a wait time, repeating (b) and (c) one or more times, wherein at least two of the repetitions have a varied wait time; and e) analyzing the detected magnetic resonance signals to extract information about the flowing fluid. To eliminate any remnant magnetization, the group of pulses may include an rf spoiler pulse.

Variable wait time measurements may also be used to measure the flow rate of a fluid by monitoring the change of frequency of the detected signals between wait times.

Alternatively, flow rate of a fluid may be determined by: a) flowing the fluid through a static magnetic field having a magnetic field gradient; b) applying a group of oscillating magnetic field pulses, each group of pulses comprising an initial pulse and one or more refocusing pulses; c) detecting magnetic resonance signals from the flowing fluid such that odd and even echoes are separately measured; d) analyzing the phase or amplitude of the odd and even echoes to determine the flow rate. One skilled in the art would recognize that the free induction decay following the initial pulse may be regarded as an "even echo" for this measurement; however, it is preferable to not use it in the measurement.

Because turbulence can affect some fluid flow rate measurements, it may be preferred to further monitor the onset of turbulence in the flowing fluid. The onset of turbulence may be monitored by comparing the amplitude of an earlier detected echo to one or more subsequent echoes, most preferably, the first echo is compared to later echoes.

The method of the present invention is particularly useful in downhole environments; however, it may also be practiced on samples in a laboratory setting.

Another embodiment of the present invention discloses an apparatus for analyzing a fluid in a downhole environment comprising: a) means for extracting the fluid from an earth formation into a flow channel within a well logging tool; b) means for generating a static magnetic field within the flow channel; c) means for generating one or more groups of oscillating magnetic field pulses to the fluid in the flow channel, wherein each group of pulses is comprised of an initial pulse followed by one or more refocusing pulses and wherein at least two of the groups of pulses are generated after a varied wait time; d) means for detecting magnetic resonance signals; and e) means for analyzing the detected magnetic resonance signals. Again, to eliminate any remnant magnetization, the group of magnetic field pulses may include an rf spoiler pulse.

Further details, features and embodiments of the invention will become more readily apparent from the detailed description that follows.

BRIEF DESCRIPTION OF THE DRAWINGS

FIGS. 3(a)–(d) are graphical representations of variable wait time data with normalized (signal) magnitude at the first echo peak as a function of wait time grouped by average flow speed.

In FIG. 6(b) all signals have been normalized to the longest wait time (400 ms) data.

DETAILED DESCRIPTION

1. Variable Wait Time Measurement Methodology

Variable wait time (VWT) measurements allow $T_1$ measurements to be made on flowing samples. These measurements allow for fluid characterization (such as during pumpout) and flow rate calculations.

Figure 1:
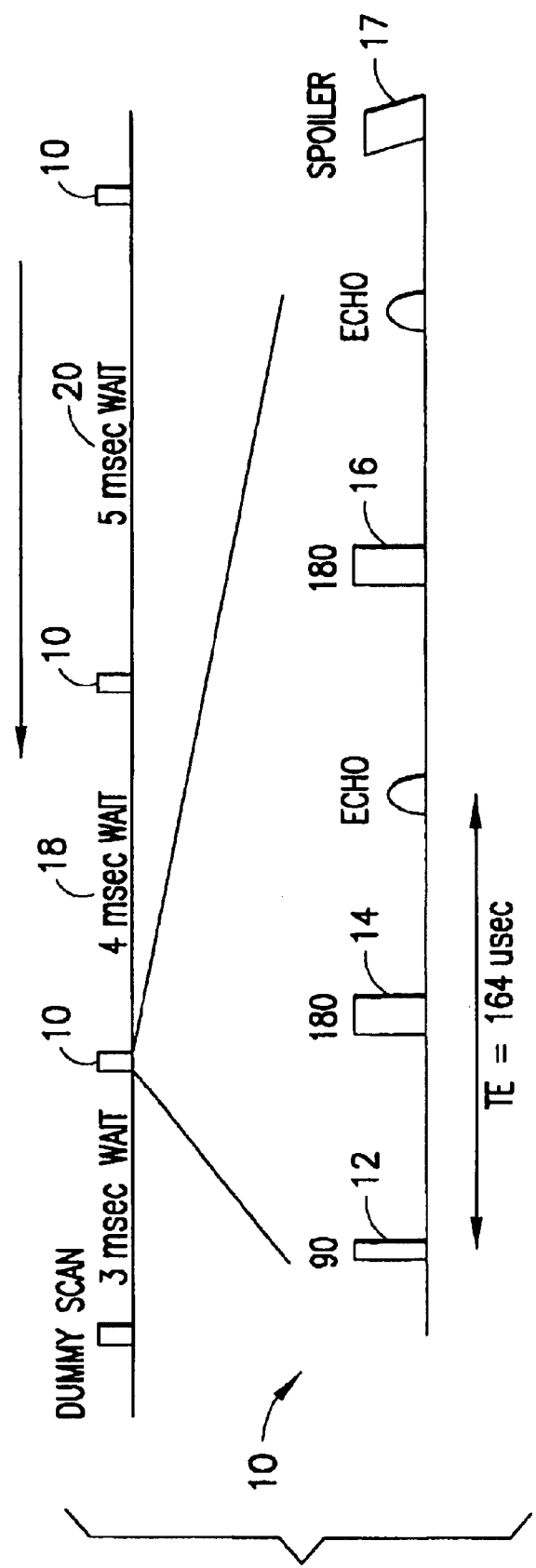
FIG. 1 is a diagram showing a non-limiting exemplary pulse sequence used for the variable wait time measurements.
Figure 2A:
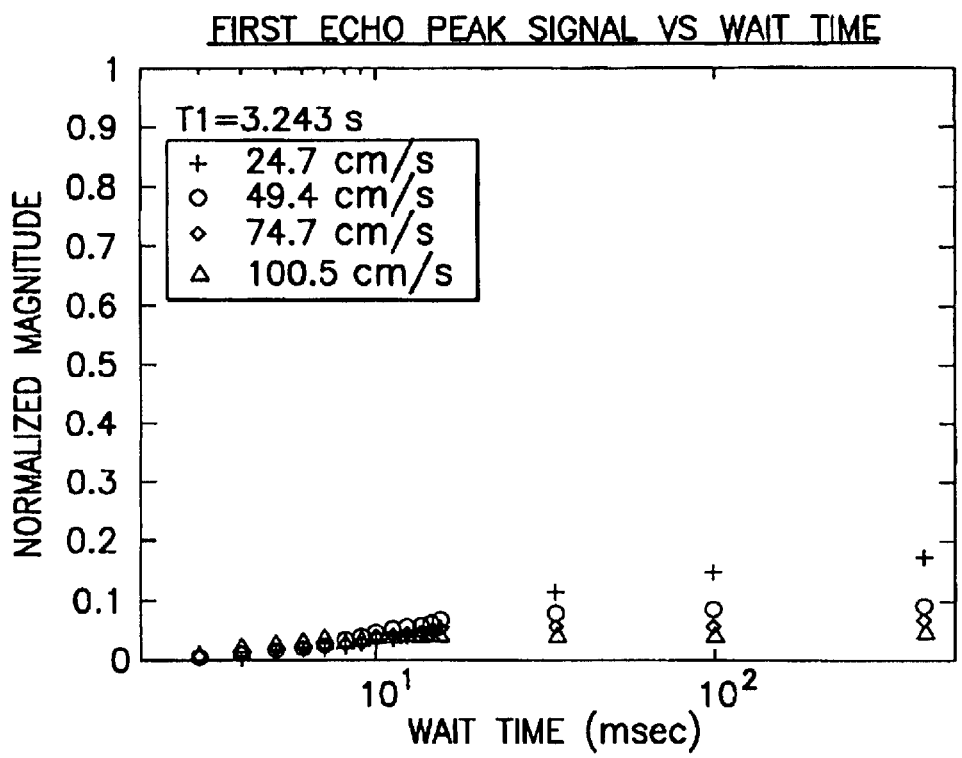
FIGS. 2(a)–(f) are graphical representations of variable wait time data with normalized (signal) magnitude at the first echo peak as a function of wait time grouped by $T_1$.
Figure 2B:
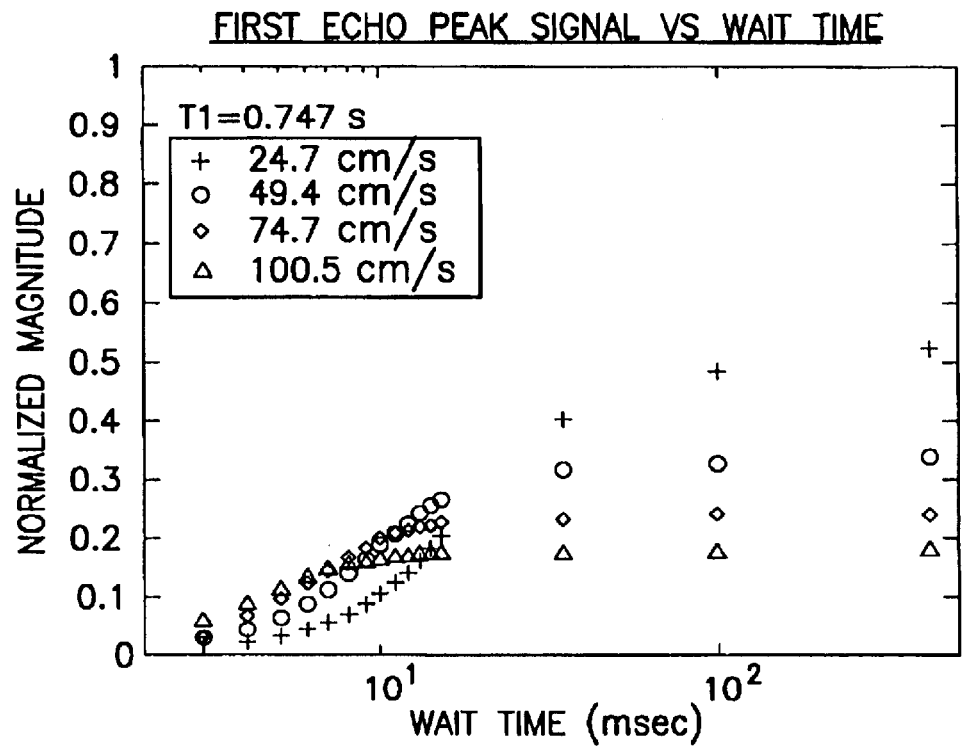
Figure 2C:
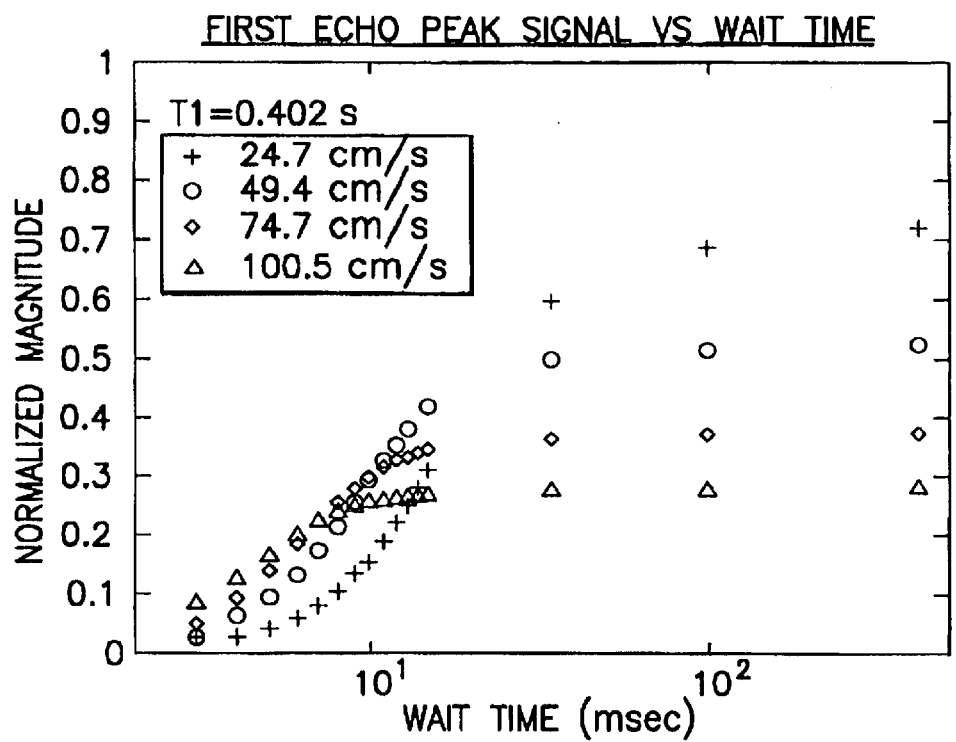
Figure 2D:
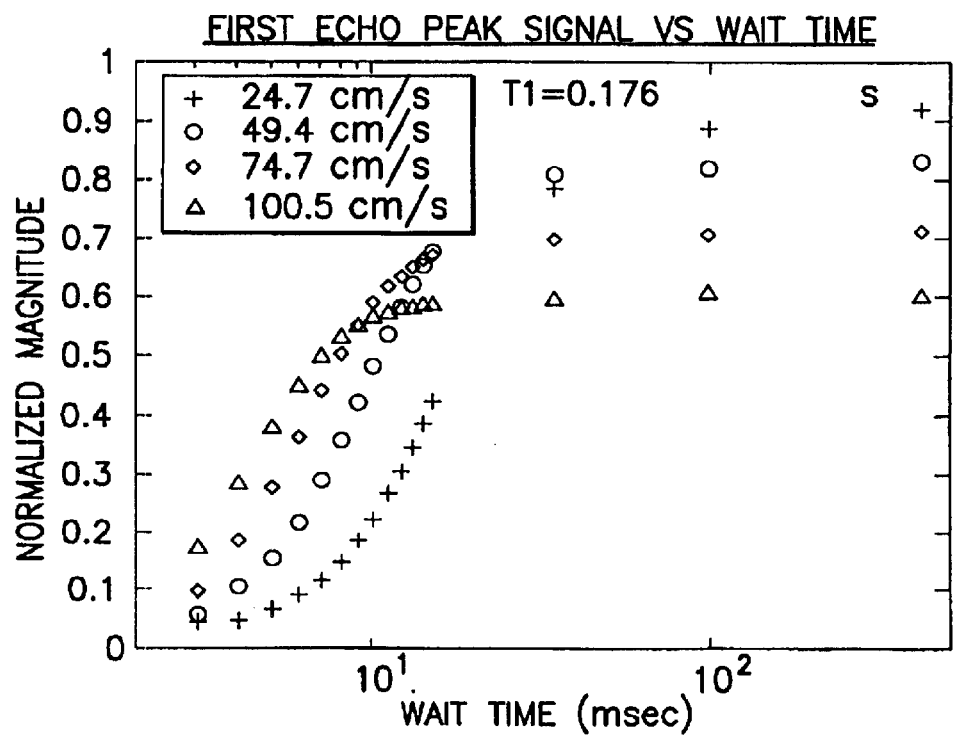
Figure 2E:
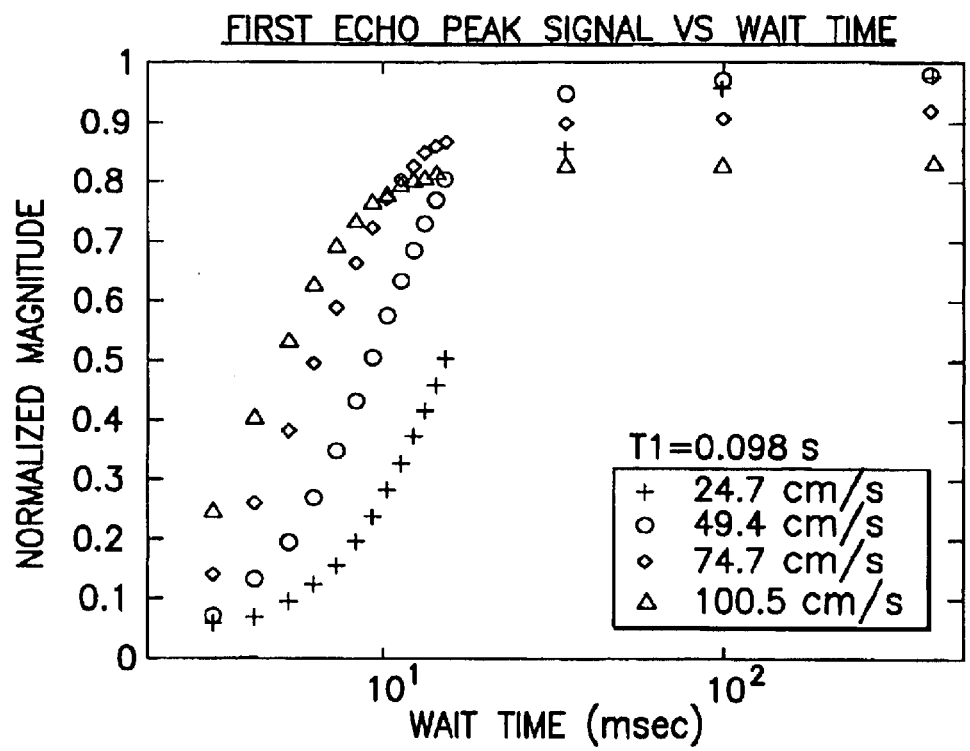
Figure 2F:
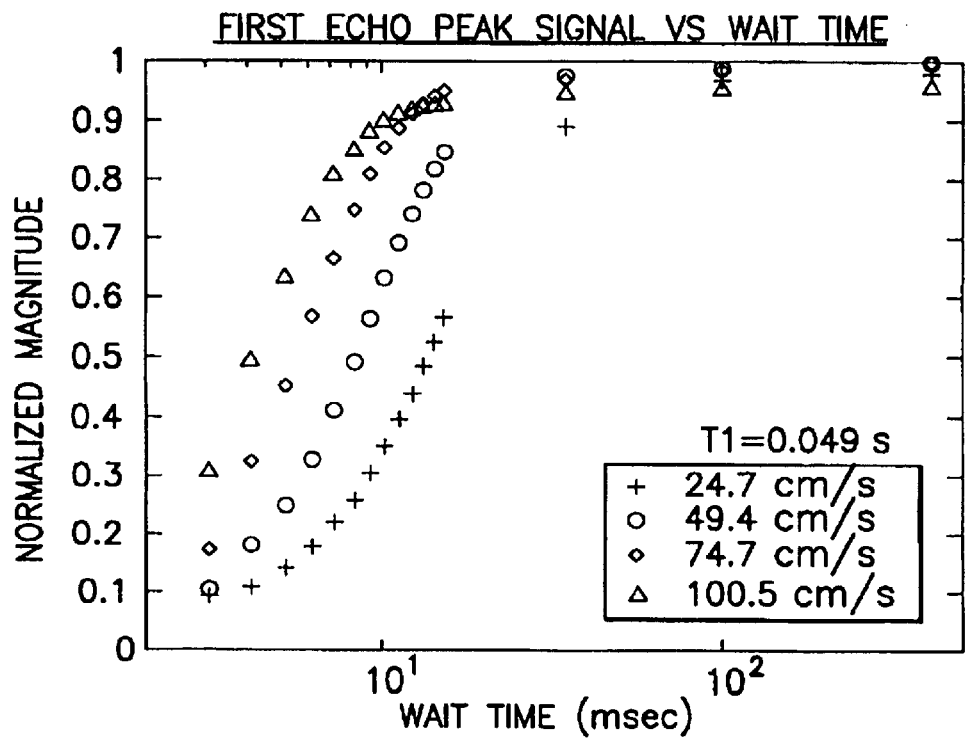
Figure 3B:
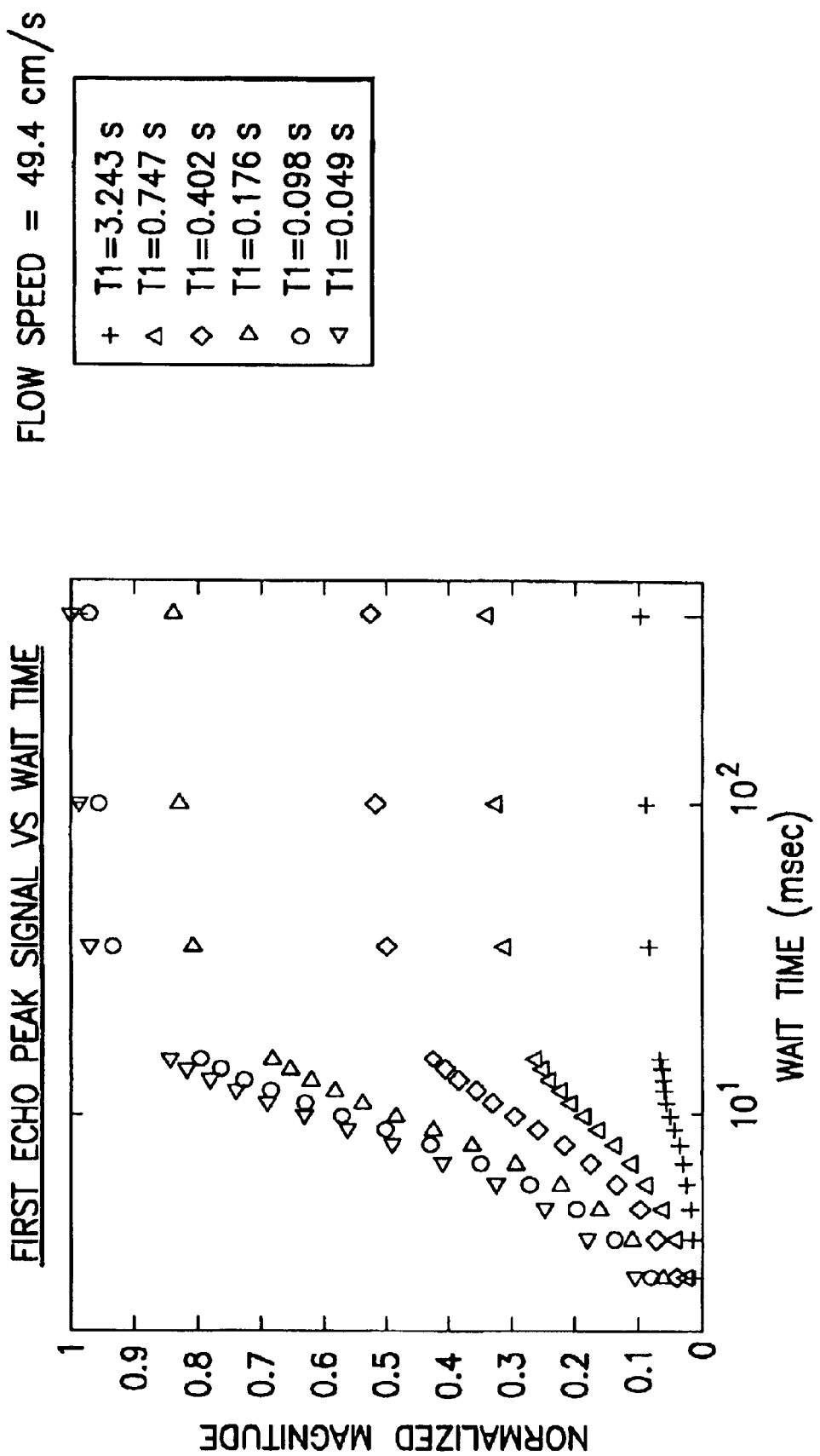
Figure 3C:
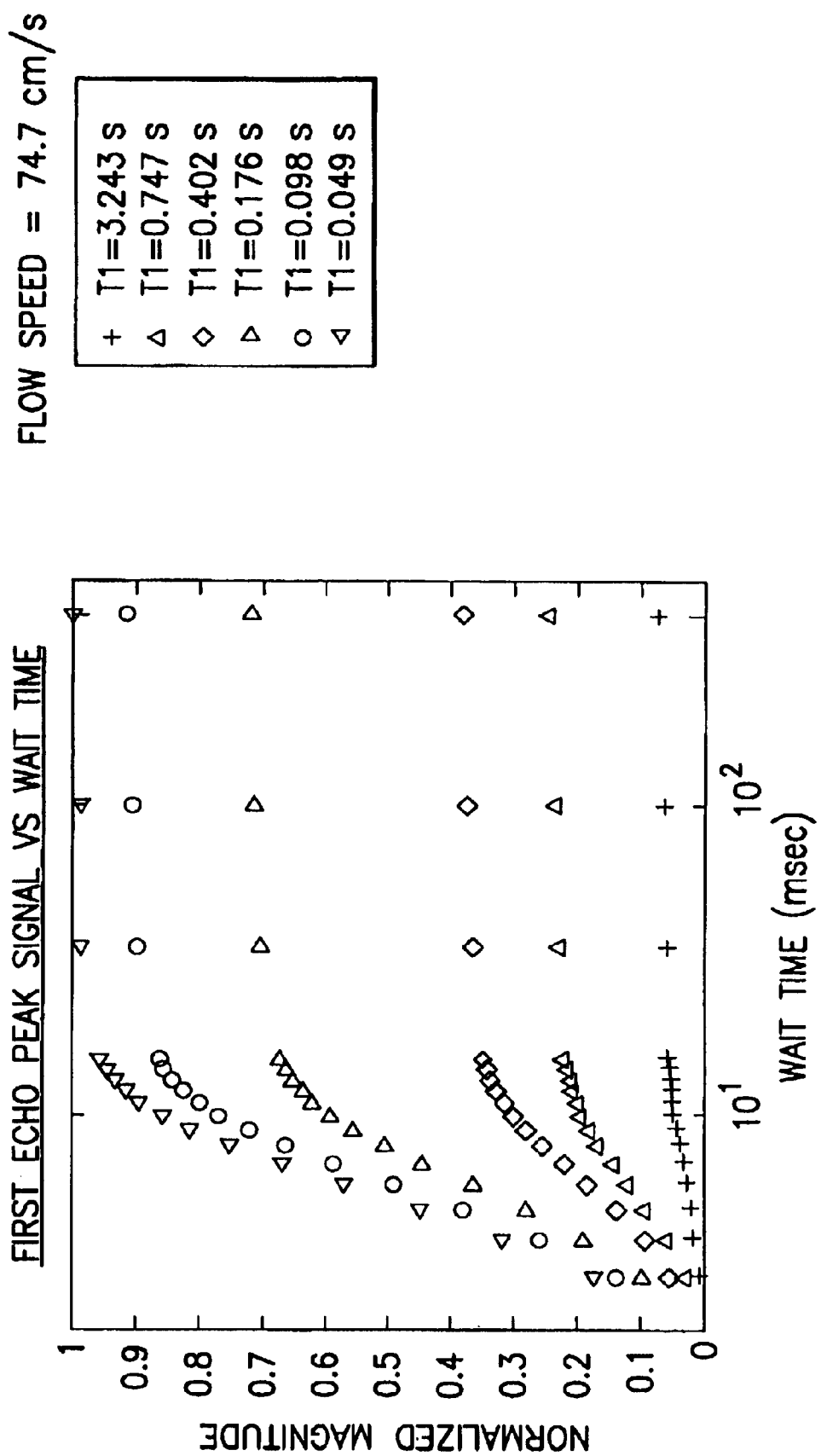
Figure 3D:
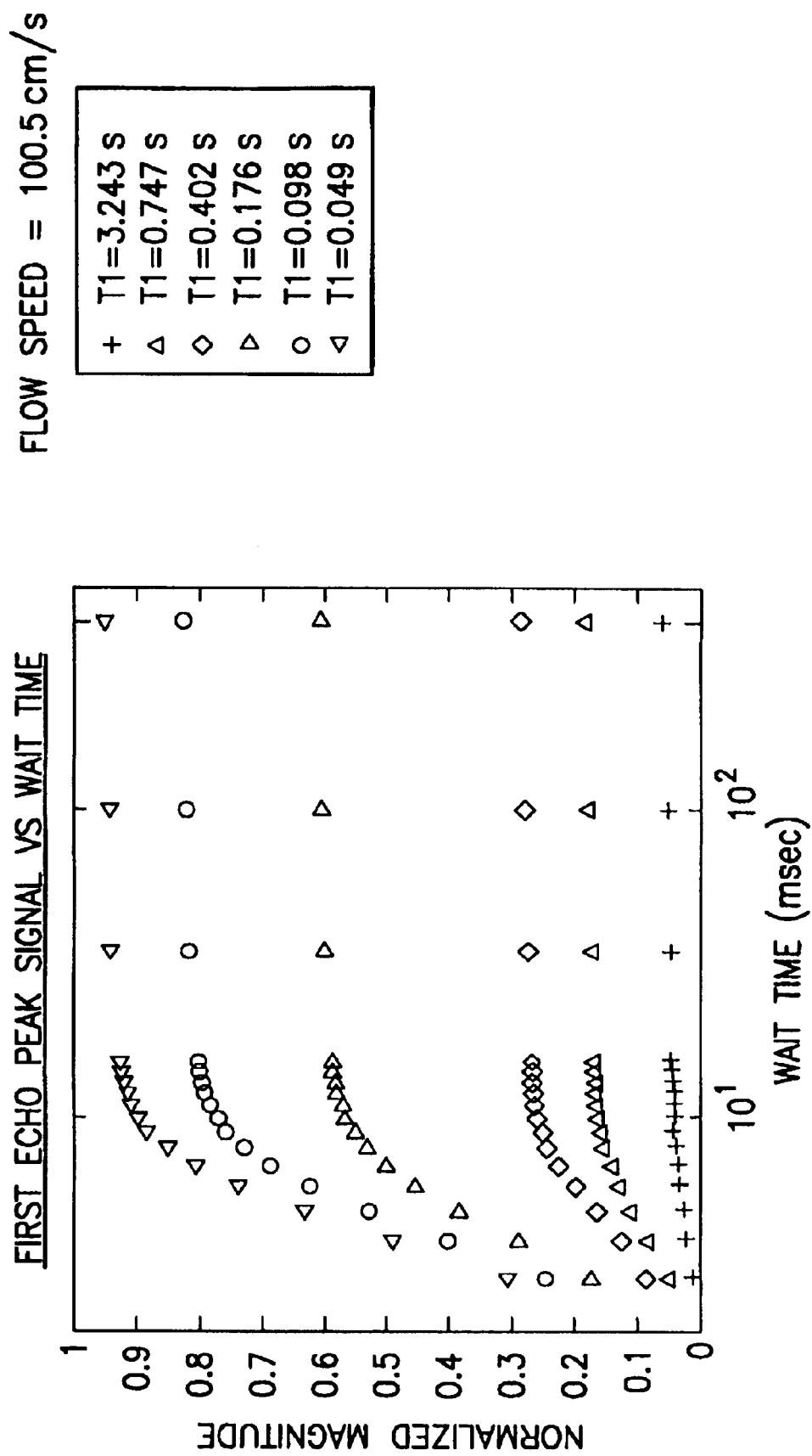

FIG. 1 shows a non-limiting pulse sequence useful in the present invention. In this example, each group of pulses 10 is comprised of an initial pulse 12 and two refocusing pulses 14, 16 with an echo spacing, $T_E$, (in this case, $T_E$ equal to 164 $\mu$s) as shown in the lower line of the figure. While two refocusing pulses are shown in the illustrated embodiment, in practice one or more refocusing pulses may be used. Furthermore, one skilled in the art would recognize that alternative echo spaces may be suitably employed. (Because rf pulses are applied in the presence of a rather large static field gradient (~100 G/cm), the flip angle and phase of the resulting mutations vary widely. Therefore, pulses in the CPMG traditionally called 90 degree and 180 degree pulses will be referred to as the initial and refocusing pulses, respectively.) Echoes may be acquired after each refocusing pulse, but it may be preferable to use the first in the analysis. Each packet of pulses (e.g., the initial pulse plus one or more refocusing pulses) not only acquires data, but also spoils the magnetization for the subsequent measurement. To ensure that the magnetization is completely spoiled after each packet of pulses, one may further apply an rf spoiler pulse 17 at the end of each pulse packet. For the purposes herein, a spoiler pulse is comprised of one or more rf pulses that, in general, can have different durations and frequencies. The latter are selected to ensure that any remnant magnetization that might exist at the end of a pulse packet is reduced to essentially zero prior to starting the wait time that precedes the next packet. The choice of the spoiler pulse is instrument-dependent because the remnant magnetization is determined, in part, by the spatial gradients in the static and rf magnetic fields. For a given instrument, the appropriate spoiler pulse can be determined empirically such that a pulse packet with a wait time of zero produces echoes with zero or negligible amplitudes. Wait times 18, 20 between the measurements allow magnetization to increase in the coil by repolarizing spoiled spins and by replacing spoiled spins with "fresh" spins whose level of polarization will depend on flow speed and $T_1$. In some cases, it may be preferable to use progressively longer wait times, as shown in FIG. 1. The use of varied wait times allows close monitoring of magnetization buildup regardless of flow speed and may be used as a means of measuring fluid properties (i.e., $T_1$ measurement) and velocity, as discussed below. Sparser measurements, which may be logarithmically spaced, may also provide good results in less time.

Measurements were made at four average flow speeds representative of typical tool pumpout rates (namely, 24.7, 49.4, 74.7 and 100.5 cm/s) for six aqueous solutions having different $T_1$ values. The $T_1$ values were determined independently via inversion recovery as was the equilibrium magnetization, $M_0$. In the tool, $M_0$ can be predetermined by calibration, as discussed below. $T_1$s ranging from 0.049 to 3.24 seconds were achieved by doping water with ferrous sulfate ($FeSO_4$). FIGS. 2(a)–(f) plot the data in $T_1$ families and FIGS. 3(a)–(d) plot the data in families of constant average flow speed. These figures show that at each of the measured flow speeds, each $T_1$ curve is distinct from all others.

Figure 4:
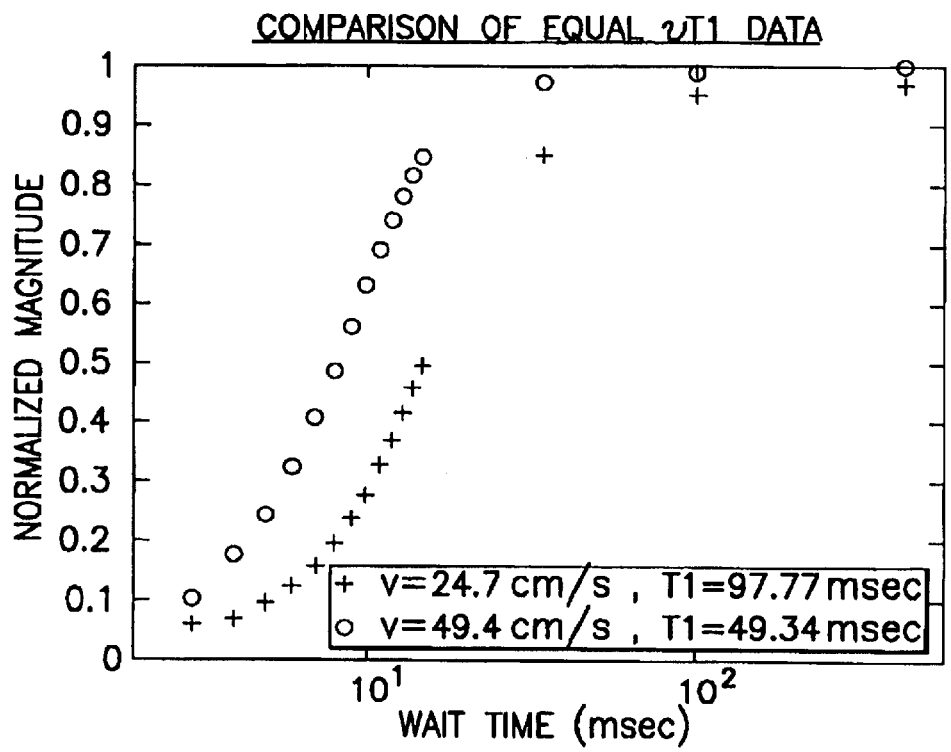
FIG. 4 is a graphical representation of two variable wait time data sets whose $\upsilon \cdot T_1$ products are equal.

Initial polarization buildup is determined by flow speed $v$, polarization length $l_p$ (essentially the distance traveled in the magnet before reaching the rf coil), and $T_1$. As shown in FIG. 4, two data sets with equal $v \cdot T_1$ products can have distinctly different curves even though the relaxation times only differ by a factor of two. Accordingly, polarization is also available from another source, namely repolarization of depleted magnetization in the coil. With a good measure of average flow speed, $T_1$ is clearly extractable.

While this methodology and the following paragraphs are directed to nuclear magnetic resonance measurements, one skilled in the art would recognize that electron spin resonance (ESR) measurements may also be employed in accordance with the present invention.

Modeling and Inversion of VWT Data

A simple model of the VWT system looks at the static and rf magnetic fields, $B_0$ and $B_1$, as either zero or full strength. In this model, spins in the fluid enter the $B_0$ field and traverse the polarization length, $l_p$, before entering the rf coil whose field is $B_1$ over a length $l_c$. For the laboratory experiments, the rf coil was 20 cm from the upstream end of the magnet and this was used as $l_p$; $l_c$ was taken to be 1 cm. Spins within the coil are assumed to see perfect 90 degree and 180 degree pulses, and magnetization exposed to a packet of pulses is considered completely spoiled, i.e. $M_x=M_y=M_z=0$. In this model, the magnetization is given by $$M = M_0\left[\left(1 - e^{\frac{-l_p}{vT_1}}\right)f + \left(1 - e^{\frac{-W}{T_1}}\right)(1-f)\right] \quad (1)$$

where f equals $\min(v_0 W/l_c, 1)$ and represents the fraction of "fresh" spins entering the coil since the last packet of pulses; W is the wait time; and $v_0$ is the average flow speed.

This simple model may be refined to account for the distribution of velocities within the flowline as well as spatial variations in the $B_0$ and $B_1$ fields.

Laboratory Calibration: Inversion Recovery

Figure 5:
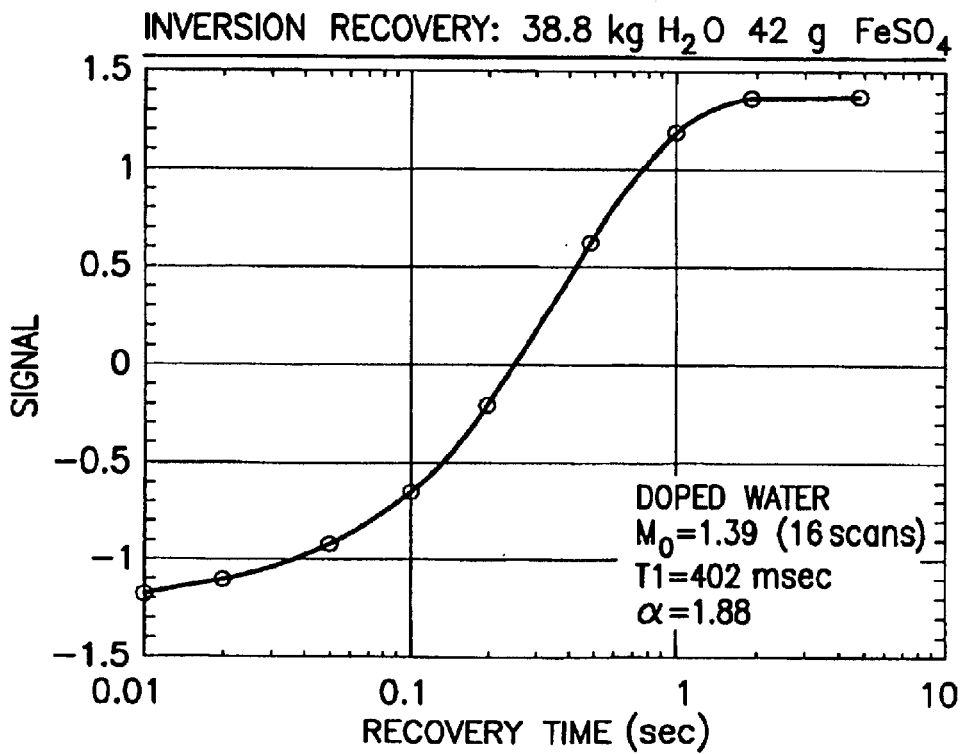
FIG. 5 is a graphical representation of the results typical of the inversion recovery measurements made in connection with the variable wait time measurements; the inversion recovery measurements provide the calibrations of the equilibrium magnetization, $M_0$, and inversion parameter, $\alpha$, and the comparison standard for the longitudinal relaxation time, $T_1$.

To validate the VWT methodology presented herein, inversion recovery measurements were performed on a static sample with each level of doping in conjunction with the VWT measurements. These measurements were used to determine the benchmark $T_1$ and $M_0$ value of each sample. The inhomogeneity of the $B_0$ field ($\Delta B_0 > B_1$) meant that the bandwidth excited by the first rf pulse was greater than that excited by the refocusing pulse. To account for this fact, the inversion recovery data were plotted for the on-resonance component only. The on-resonance signal was obtained by Fourier transforming the complex time domain data. The magnitude of the on-resonance signal was fit to $$M(t)=M_0(1-\alpha \exp(-t/T_1)) \quad (2)$$

where $M_0$, $T_1$, and $\alpha$ are free parameters. Ideally, one would expect $\alpha=2$, but imperfect pulses in an inhomogeneous static field result in slight variations. Table 1 shows the results of the measurements; FIG. 5 plots typical data.

TABLE 1

Results of Inversion Recovery Experiments

| Concentration $FeSO_4$ (ppm) | Equilibrium Magnetization, $M_0$ | Longitudinal Relaxation Time, $T_1$ (ms) | Inversion Parameter $\alpha$ |
|---|---|---|---|
| 0 | 1.46 | 3240 | 1.81 |
| 560 | 1.46 | 747 | 1.83 |
| 1081 | 1.39 | 402 | 1.88 |
| 2630 | 1.26 | 176 | 1.90 |
| 5120 | 1.25 | 98 | 1.83 |
| 9720 | 1.25 | 49 | 1.84 |

2. Velocity and Flow Regime Measurements

Measurement of flow speeds in a fluid sampling tool, such as Schlumberger's MDT™ is important for dynamic NMR and has independent importance as well. Flow speed affects the level of polarization of the sample when it reaches the NMR sensor. Therefore, accurate flow speed determination is very valuable. Flow line NMR measurements are capable of giving quantitative and qualitative information about the flow velocity or the flow regime. These measurements rely on the existence of a static magnetic field gradient. Motion in the presence of that gradient is clearly discernible in the observed signal.

Time-of-Flight

Figure 6A:
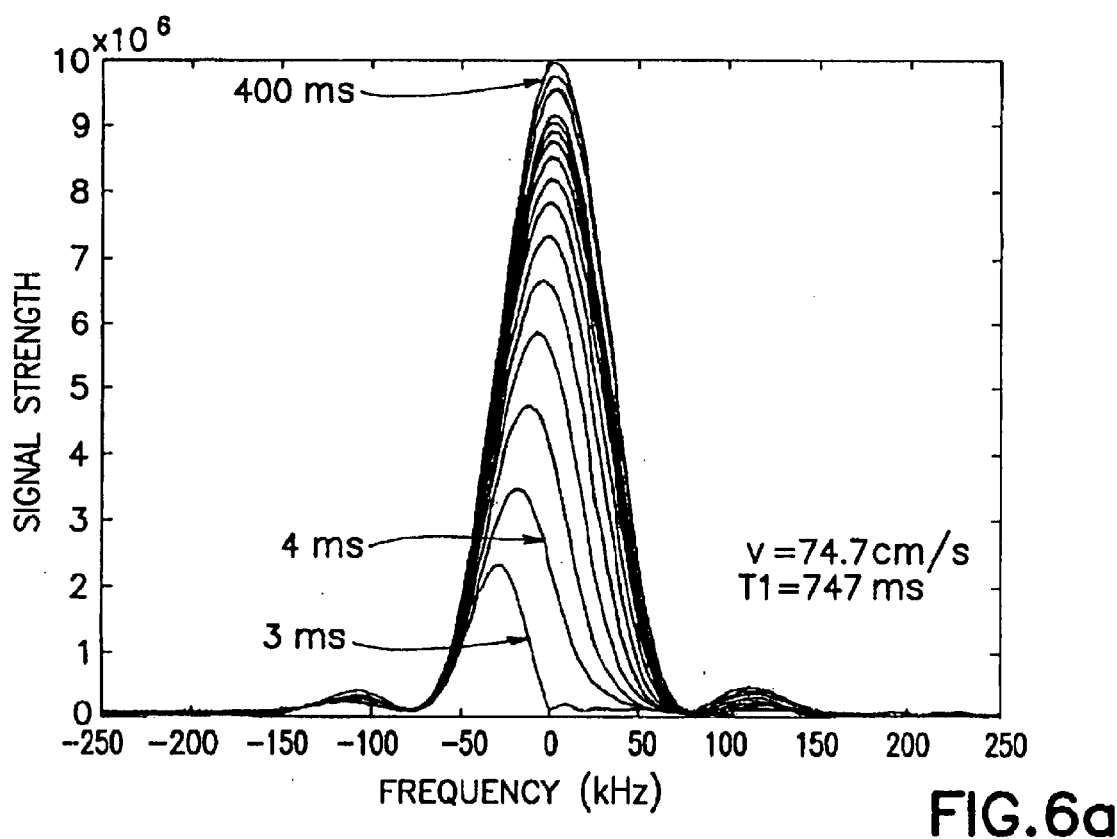
FIGS. 6(a)–(b) are graphical representations of variable wait time data displayed in the frequency domain and display time-of-flight behavior. Curves are for wait times ranging from 3 ms to 400 ms for $FeSO_4$-doped water ($T_1$=747 ms) flowing at 74.7 cm/s through a magnetic field gradient.
Figure 6B:
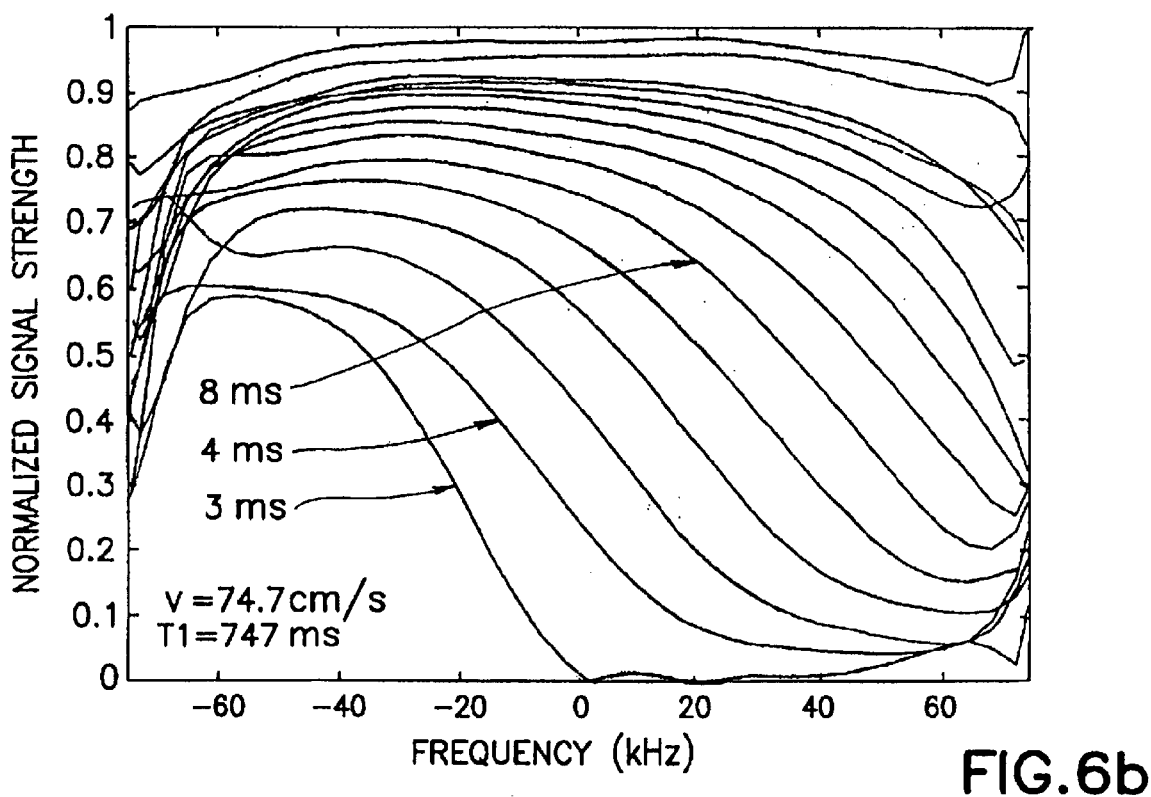

By saturating the spins in the rf coil (such that magnetization is spoiled and there is no detectable signal), waiting a predetermined period of time, and detecting the resultant echo, the movement of "fresh" spins into the coil may be observed when the $B_0$ field gradient has a component in the direction of fluid flow. Repeating this process with a number of different wait times allows the flow of fluid through the rf coil to be monitored. FIG. 6(a) shows VWT data transformed into the frequency domain, while FIG. 6(b) shows the same data normalized to the longest wait time tested (400 ms). The signal is observed to move from left to right across the figure for the embodiment shown therein. Calibration of rate of frequency change allows one to measure the flow speed. To the first order, the frequency change is defined as $\Delta\omega=\gamma Gv\Delta t$, where G is the magnitude of the gradient in the direction of flow, v is the flow speed and $\Delta t$ is the difference between wait times where two measurements are made. If more than two measurements are made, $\Delta t$ may be calculated by fitting the data. Based on FIG. 6(b), the gradient in the direction of flow is about 50 G/cm for this sample.

Odd-Even Echo Phase Difference for Velocity

When the magnetization of a sample has a component transverse to the local magnetic field, it will precess at its Larmor frequency. In the laboratory frame, the spins will acquire phase according to $$\varphi = \int \omega dt \quad (3)$$

$$= \int \gamma(B_0 + \Delta B_0) dt \text{ (free precession)}$$

where ω is the angular frequency, γ is the gyromagnetic ratio, $B_0$ is the mean static magnetic field and $\Delta B_0$ accounts for any local variation in that field. If $\Delta B_0$ equals G·r, then in the reference frame rotating at the receiver frequency (set to the Larmor frequency) with respect to the lab, the phase accumulated for a first echo is $$\varphi = \gamma G \left[ -\int_0^{\frac{TE}{2}} (x_0 + v_0 t + \ldots) dt + \int_{\frac{TE}{2}}^{TE} (x_0 + v_0 t + \ldots) dt \right] \quad (4)$$

where G is the magnetic field gradient in the direction of the flow, and $v_0$ is the average flow speed. Thus, for the first echo (and all subsequent odd echoes), the phase accumulated by a spin moving at constant velocity is $$\phi = +\gamma G v_0 TE^2/4 \quad (5)$$

For flows where the velocity distribution is symmetric about the mean equation (5) holds for the observed signal. Such is the case for laminar flow. Under the same circumstances, the phase accumulated for an even echo is zero. Thus, the phase difference between odd and even echoes is proportional to the flow speed when the higher order terms in the expansion of position are zero. This condition is met for laminar flow.

Figure 7:
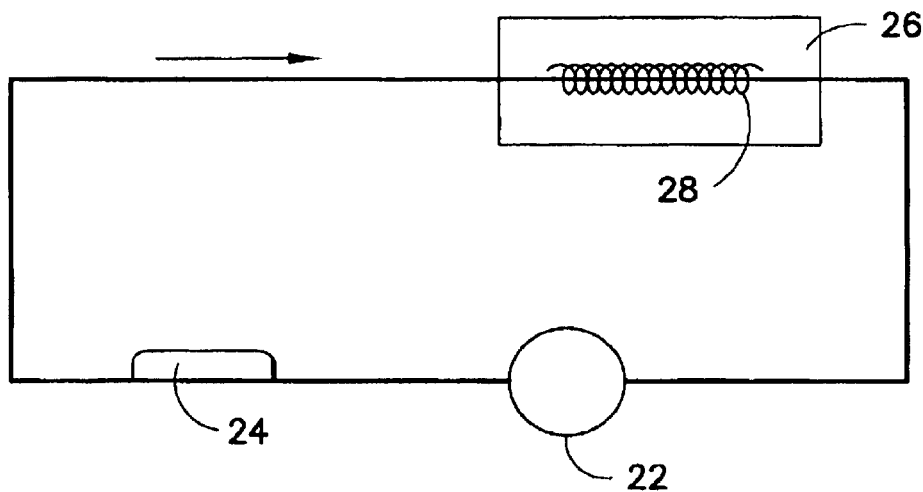
FIG. 7 is a schematic diagram of a flow system used for one of the laboratory experiments.
Figure 8:
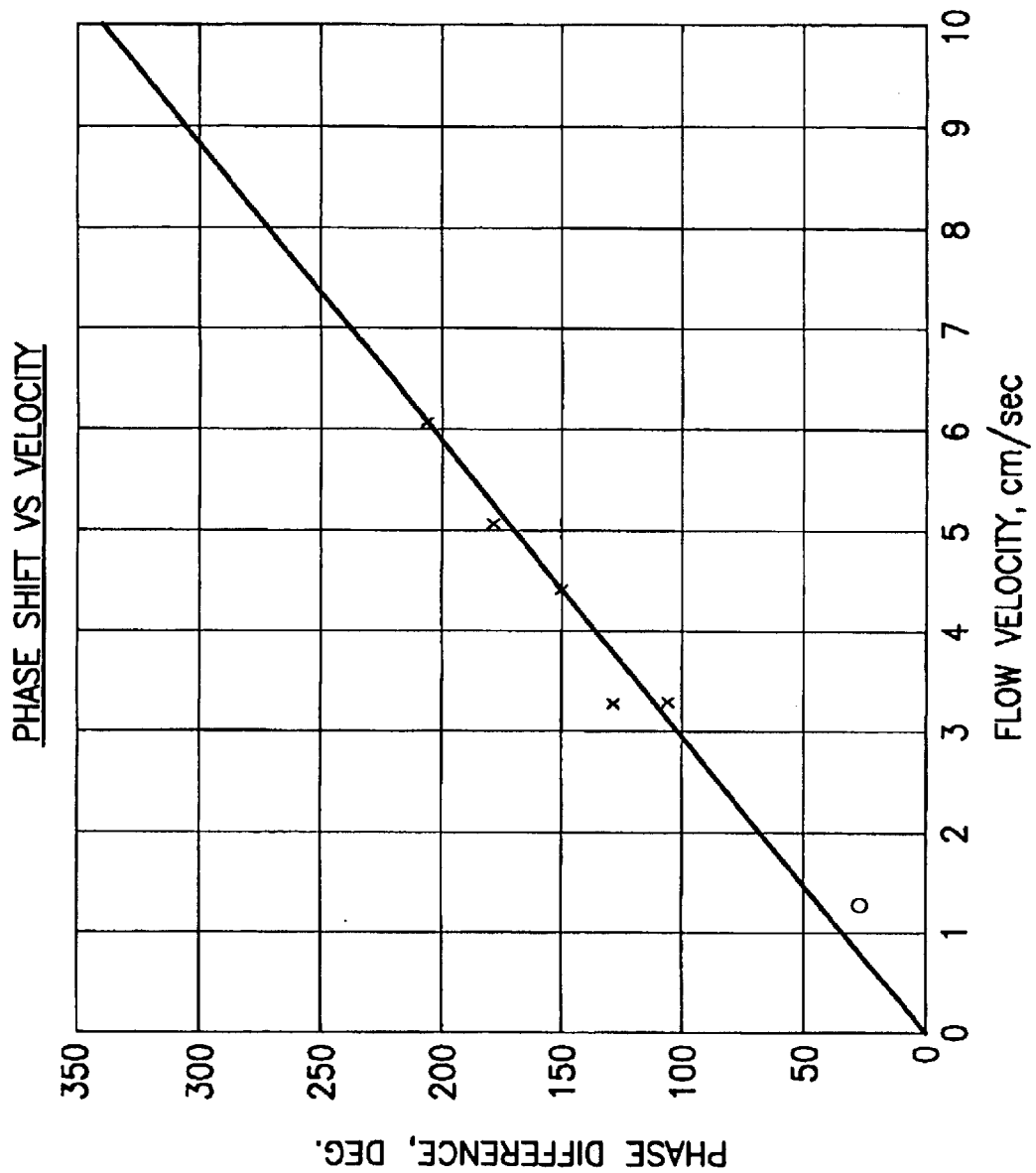
FIG. 8 is a graphical representation of the phase difference between odd and even echoes of a CPMG experiment as a function of average flow velocity for low speed non-turbulent flows.
Figure 9:
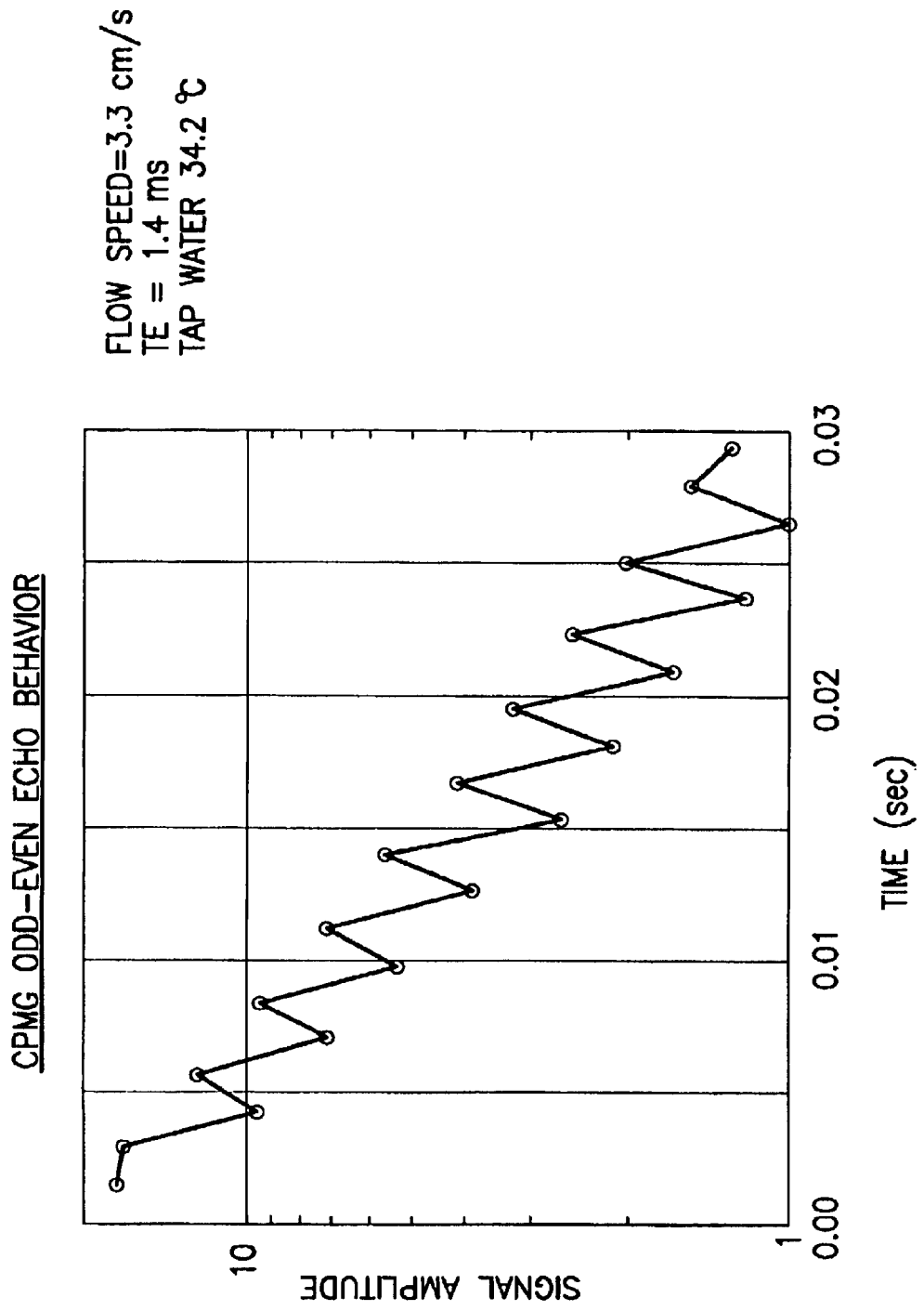
FIG. 9 is a graphical representation of the CPMG echo amplitude behavior with flow in a static magnetic field gradient, wherein the decay of the even echoes is due only to irreversible microscopic relaxation process and odd echoes are reversibly defocused by flow in the magnetic field gradient.

This approach was tested at flow speeds up to 6 cm/s as shown in FIG. 7. The laboratory flow system for this test comprises a peristaltic pump 22 that flows the sample fluid. Flow is steadied using a pulse dampener 24 designed to remove pulsatile motion. The sample flows through the magnet 26 and rf coil 28. Pump rates were calibrated by flowing the sample into a graduated cylinder. FIG. 8 shows the linear relationship between odd-even echo phase difference and velocity. FIG. 9 demonstrates the loss of odd-echo signal amplitude due to motion-related dephasing during a CPMG.

Figure 10:
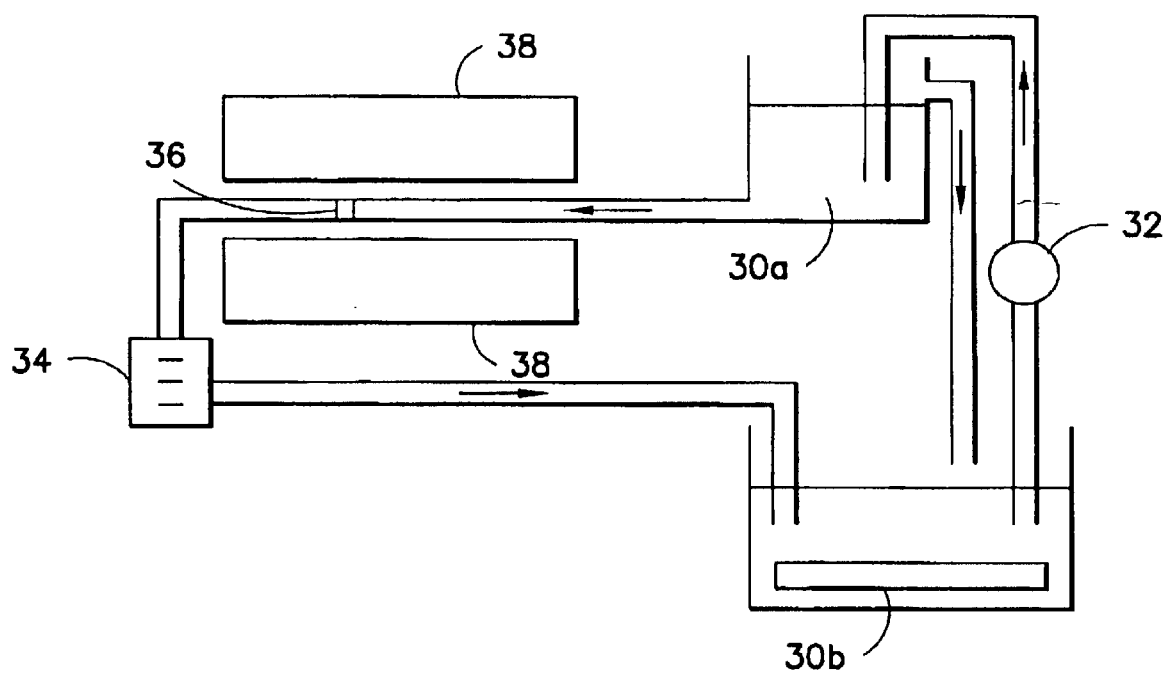
FIG. 10 is a schematic diagram of a second flow system used for the laboratory experiments.

At higher flow speeds, laminar flow with its constant-velocity streamlines breaks down and turbulence develops. Turbulence introduces higher order motion moments and even-echo gradient moment nulling no longer returns the accumulated phase to zero. In such cases, phase difference is not an adequate velocity indicator. Accordingly, it may be desirable to monitor the flowline for the onset of turbulence.
Ratio of First to Later Echoes as Indicator of Flow Speed/Reynolds Number The Reynolds number is given by $$Re = \rho L v/\mu \quad (6)$$

where ρ is the fluid density, L is the tube diameter, υ is the average flow speed, and μ is the viscosity. For water flowing at υ cm/s in the laboratory system of FIG. 10, Re equals 63.4υ at 20 degrees Celsius and Re equals 88.2υ at 35 degrees Celsius. The laboratory flow system shown in FIG. 10 comprises two reservoirs 30a, 30b maintaining a pressure head of about 1 m. Return from the lower reservoir 30b to the upper 30a may be achieved using a pump 32 and a constant pressure head may be established by returning overflow to the lower reservoir 30b. Flow rates may be determined using a flow meter 34 and controlled with a needle valve. Flow through the magnet 38 is through a 0.64 cm (0.25 inch) ID, 0.95 cm (0.375 inch) OD PVC tube having rf coil 36. The transition to turbulence is generally accepted to occur at about Re equal to 2000, though values can range from 1500 to 3000 at the onset of turbulence.

Figure 11:
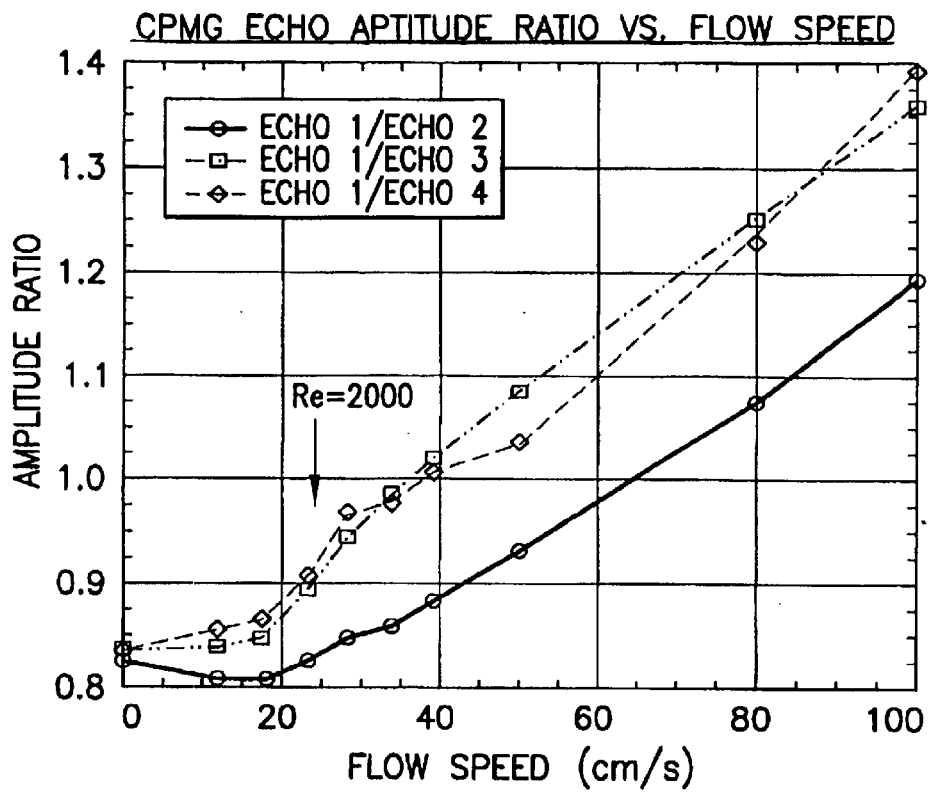
FIG. 11 is a graphical representation of the ratio of first echo amplitude to subsequent echoes in a CPMG sequence as a function of flow velocity, wherein the echo time is 164 $\mu$s.

FIG. 11 shows ratios of the amplitude of the first echo to one or more subsequent echoes in a CPMG experiment as a function of flow speed. While the first echo is preferred, other echoes may be used so long as an early echo and at least one later echo are compared. Alternatively, one may compare the amplitude of the free induction decay following the initial pulse to one or more subsequent echoes. Once the transition to turbulence occurs, these ratios grow monotonically. This trend is not primarily attributable to flushing observable magnetization out of the coil because, for these experiments, $T_E$ was equal to 164 μs. Even for the fourth echo and a 100 cm/s flow rate, the sample has moved only 0.06 cm through a 1.2-cm coil. If laminar flow is incorrectly assumed under these conditions, even the fastest spins would have moved only 0.12 cm. It is much more likely that this effect is related to the failure of magnetization to rephase completely during echo formation due to turbulent flow in the presence of a gradient. This is analogous to the loss of signal amplitude due to diffusion in a gradient for a static sample. The relatively constant ratios for flows with Re<1500, i.e., laminar flow, support this conclusion. Varying echo spacing may allow one to determine both velocity and Reynolds number in much the same manner as one determines $T_2$ and the diffusion constant for a static sample.
Independent Determination of Flow Speed An independent (non-NMR) determination of flow speed may be useful if the required level of measurement precision is not available through NMR. A likely candidate is the noninvasive acoustic time-of-flight measurement, wherein two transducers separated by a known distance alternatively send and receive acoustic signals through the flowing medium The propagation times for both directions allows determination of both the speed of sound in the fluid and the speed of the fluid. This measurement is also useful in characterizing such fluid properties as density.
3. Description of the Apparatus The following paragraphs describe an apparatus to implement the present invention. Accordingly, one skilled in the art would recognize that other configurations, loads/capacities, dimensions, etc. may be suitably employed.
Static Magnetic ($B_0$) Field Materials: The tested neodymium-iron-boron (NdFeB) magnet was manufactured by Magnet Sales of Culver City, Calif. using NdFeB from Shin-Itsu of Japan. The material grade used (N34UH) has a remanence (residual induction) of 1.14–1.20 T and a temperature coefficient of 0.09% per degree Celsius. In the 50 W system (see discussion below), the excitation bandwidth of an 11-microsecond 180 degree refocusing pulse is given approximately by the Fourier Transform theorem as 90.9 kHz. A one degree Celsius temperature change in the magnet shifts the resonance frequency by 55.8 kHz, or about 60% of the excitation bandwidth. With an intrinsic gradient of about 100 G/cm, the corresponding 2-mm excited slice is shifted by 1.2 mm. At higher power the effect may be less noticeable because most of the flow line should be excited. A samarium-cobalt (SmCo) magnet has the advantages of a smaller temperature coefficient (0.03% per degree Celsius) and higher maximum operating temperatures which may be advantageous downhole. A smaller temperature coefficient is advantageous in stabilizing the Larmor frequency of the sample, which is directly proportional to the strength of the $B_0$ field (ω=γ$B_0$).

In other cases, NdFeB is may be a preferred material as it is less brittle, is half the price and has a higher remanence at room temperature compared to SmCo.

Figure 12:
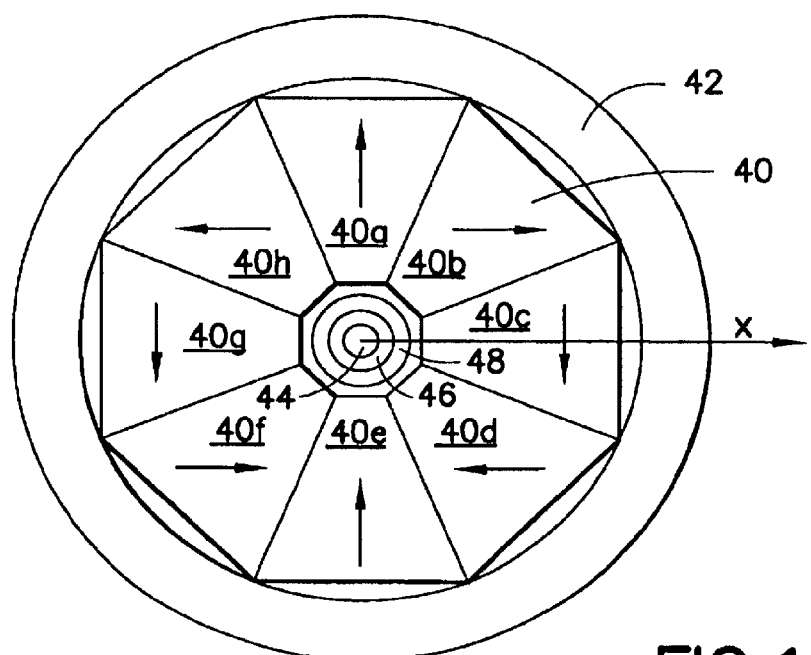
FIG. 12 is a cross-sectional depiction of the Halbach array in a sonde housing.

Design and Modeling: A 1.44 T static magnetic field was generated by a Halbach array rare-earth permanent magnet, as described in "Design of Permanent Multipole Magnets with Oriented Rare Earth Cobalt Material," *Nuclear Instruments and Methods* 169, 1–10 (1980) by K. Halbach and "Physical and Optical Properties of Rare Earth Cobalt Magnets," *Nuclear Instruments and Methods* 187, 109–117 (1981) by K. Halbach, incorporated by reference herein in their entireties. The design approach was two-dimensional and assumed a large extent in the axial direction relative to the aperture of the magnet. FIG. 12 shows a non-limiting embodiment of a suitable design in cross-section. Arrows indicate the orientation of the easy axis for each magnet segment. The governing equations are $$\underline{B}^*(z_0) = B_r \sum_{v=0}^{\infty} \left(\frac{z_0}{r_1}\right)^{n-1} \frac{n}{n-1} \left[1 - \left(\frac{r_1}{r_2}\right)^{n-1}\right] C_n, \tag{7a}$$

$$n = N + vM, \tag{7b}$$

$$C_n = \frac{\cos^n(\pi/M)\sin(n\pi/M)}{(n\pi/M)}, \tag{7c}$$

$$\left\{\frac{n}{n-1}\left[1 - \left(\frac{r_1}{r_2}\right)^{n-1}\right]\right\}_{n \to 1} = \ln\left(\frac{r_2}{r_1}\right) \tag{7d}$$

where $\underline{B} = B_x + iB_y$ is the magnetic field, $\underline{B}^*$ is its complex conjugate, $\underline{z} = x + iy$ is position, $\underline{B}_r$ is the complex representation of the remanence vector of the reference trapezoidal block that is bisected by the positive x axis, M is the number of trapezoidal blocks per magnet (ring) and $r_1$ and $r_2$ are the distances between the coordinate origin and the intersections between the reference block and the positive x axis. For a dipole magnet, N equals 1. The easy axis orientation of each block is given by $\beta(\phi) = (N+1)\phi$ where r, $\phi$ locate the center of the block in polar coordinates. (Note that in FIG. 12, easy axes are rotated by $-\pi/2$.) The design produces a static field perpendicular to the magnet axis (upward in FIG. 12).

In order to provide an adequate polarization region upstream of the rf probe, the magnet was designed to be 30.48 cm (12 inches) long. The raw materials from which the magnet segments were cut made it preferable to construct the magnet of six substantially identical Halbach arrays, each 5.08 cm (2 inches) long in the axial dimension. As shown in FIG. 12, each array 40, is comprised of eight trapezoidal segments 40a . . . 40h (M=8) and has an inner diameter ($2r_1$) of 22.0 mm (0.870 inches) and an outer diameter ($2r_2$) of 91.0 mm (3.580 inches), both measured at the midline of the trapezoid. Thus, the maximum outer diameter (OD) of the array, measured vertex to vertex is 9.84 cm (3.875 inches), which is the inner diameter (ID) of Schlumberger's MDT™ sonde housing. Each Halbach ring 40 was placed in an aluminum housing 42, and the entire magnet was assembled by screwing the adjacent housings together. The sample within the flowline is shown as numeral 44 inside the rf antenna 46. The flowline around the antenna is shown as numeral 48.

Equations (7a) to (7d) give the static magnetic field for the ideal case. Due to manufacturing tolerances it is preferable to allow for variations of the remanence and easy axis orientation of each segment in the array. For such calculations, one may use $$\underline{B}^*(z_0) = \frac{1}{2\pi} \int \frac{B_r(z)}{(z_0 - z)^2} dxdy \tag{8}$$

where $B_r$ is the remanence of the individual segment. Manufacturing tolerances in the easy angle orientation of ±1 degree and in the remanence of ±1% were included in final modeling and indicated that one could expect inhomogeneities of about 1500 ppm in the transverse plane over the area of the flow line interior.

Validation of Product: Laboratory experiments show that a large range of measurements can be effectively made even with large $B_0$ inhomogeneities. Accordingly, it may not be critical to remove all sources of field inhomogeneity. Notwithstanding the foregoing, in some cases it may be preferable to reduce field inhomogeneity. Accordingly, it was observed that the magnet may be subject to two types of defects that may affect the field homogeneity. The first is a twist in the assembly along its axis, which is preferably corrected by the manufacturer. The second defect is chipping of the magnet, particularly on the inner surfaces at the interfaces between rings which will be discussed below.

Figure 13A:
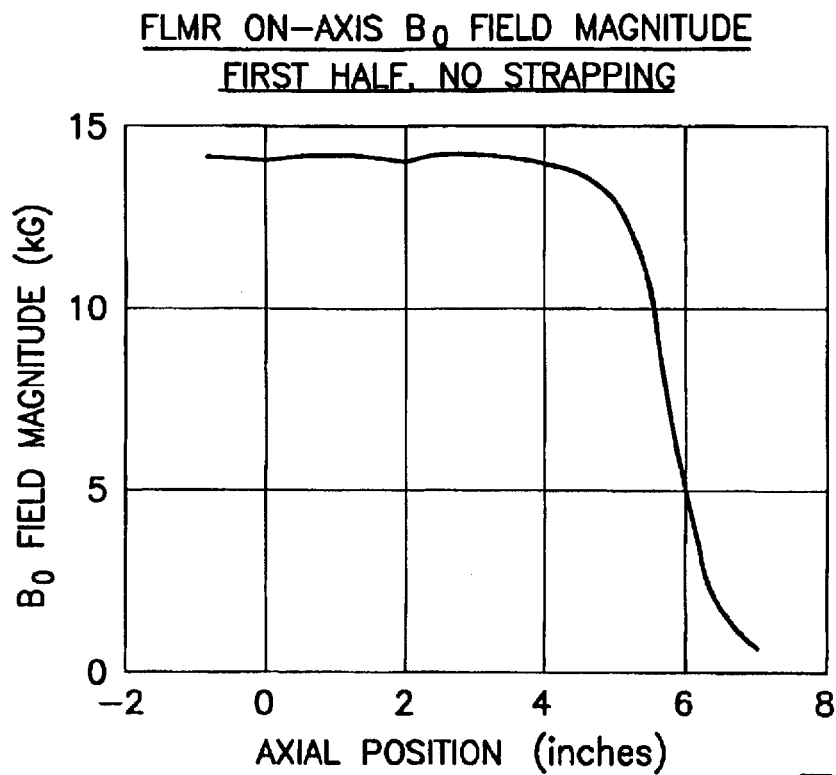
FIGS. 13(a)–(b) are graphical representations of the magnitude of the static magnetic field along the axis of the Halbach array, wherein the magnet extends –6 to 6 inches.
Figure 13B:
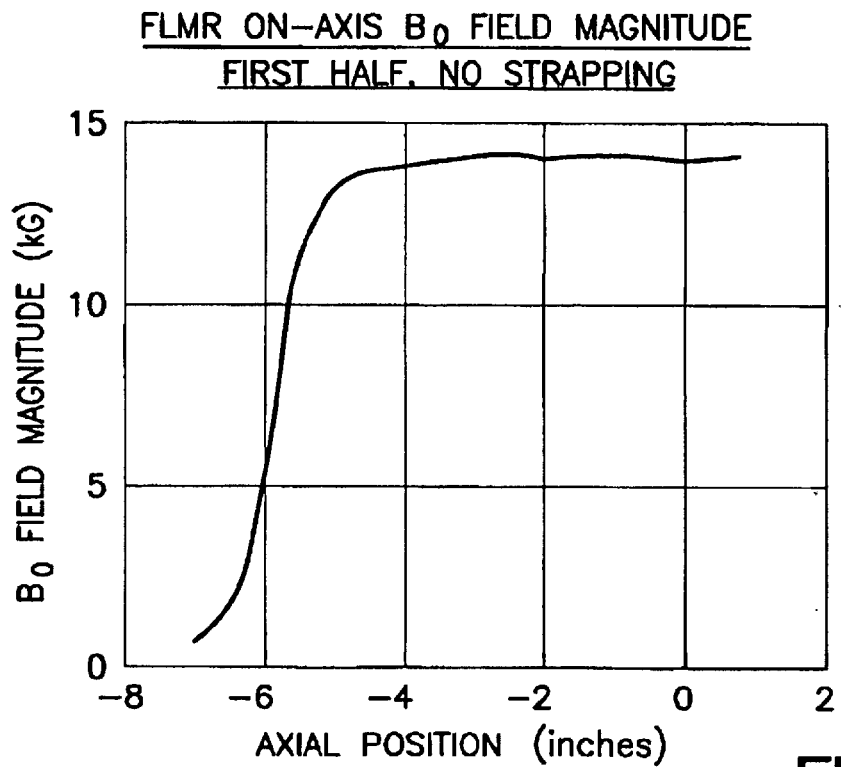
Figure 14A:
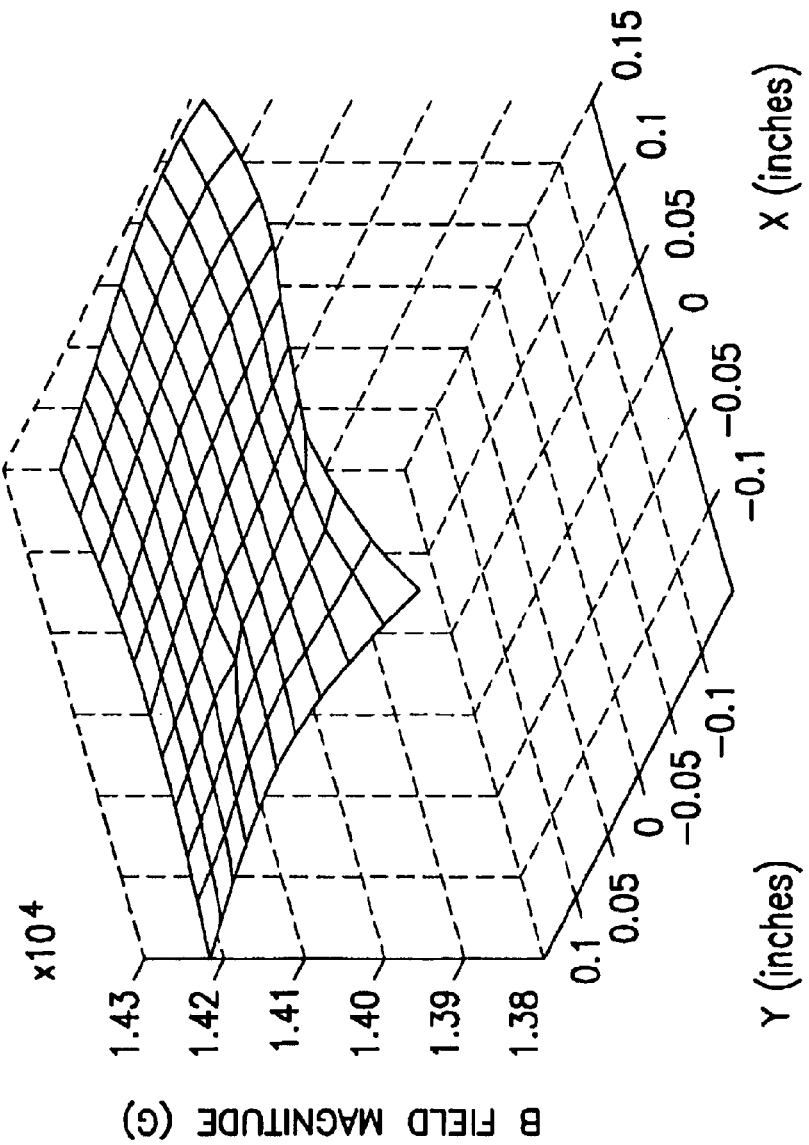
FIGS. 14(a)–(c) are three-dimensional graphical representations of the magnitude of the measured static magnetic field at three slices across the Halbach array aperture: (a) at the center of one Halbach ring, (b) at a joint between two rings and (c) at a joint with significant chipping of the magnet.
Figure 14B:
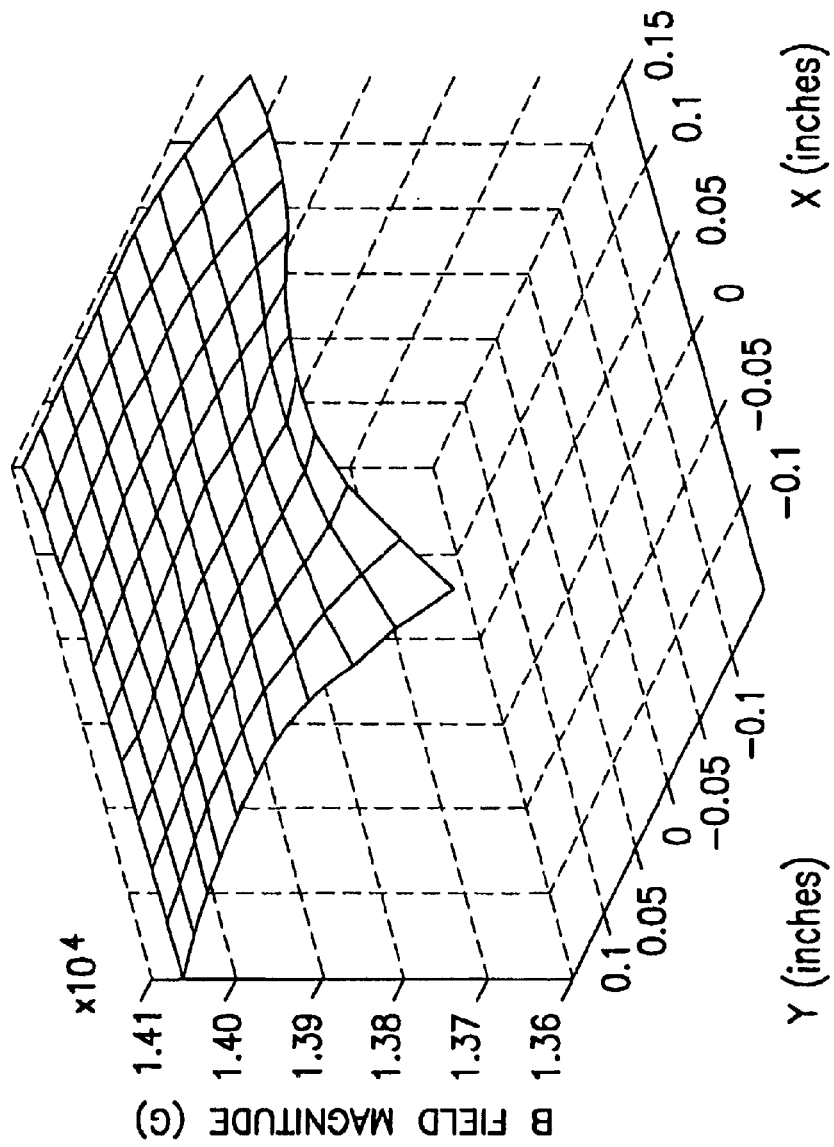
Figure 14C:
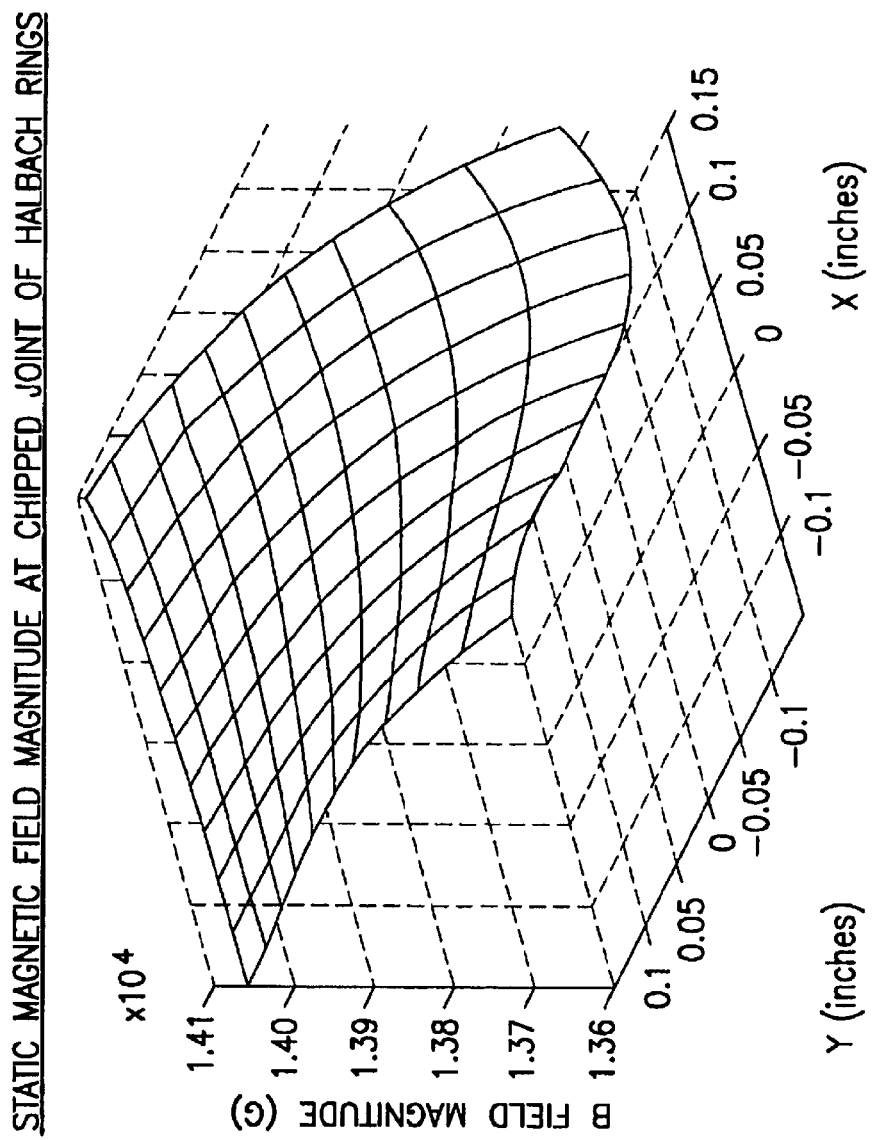

The magnetic field vector components were measured over the interior volume of the magnet and some of the fringe field using a gaussmeter (F. W. Bell, Model 9903, Orlando, Fla.) with a three-axis probe (Model 3X-99-241). The probe was designed to measure fields up to 1 T. Above that, the probe was uncalibrated and nonlinear. Because the magnetic field inside the magnet exceeded this by nearly 50%, the measurements were nonlinear and low. FIGS. 13(a) and (b) show the uncalibrated magnitude of the $B_0$ field along the axis of the magnet. Dips in the field are visible at 5.08 cm (2 inch) intervals, coinciding with joints in the assembly. These dips were as large as 200 G, giving rise to field inhomogeneities an order of magnitude larger than those estimated in the design. FIGS. 14(a)–(c) show three transverse slices of the magnetic field: one at the center of a Halbach ring, another at a joint with little chipping, and a third at a joint with severe chipping, respectively. Ignoring corners of the plots because they fall outside the flow line, the field inhomogeneity is 3100, 1600, and 28900 ppm, respectively. All but the badly chipped joints have inhomogeneities close to the 1500 ppm modeled with manufacturing tolerances. FIGS. 14(a)–(c) cover a range of 500 G, though the magnitude of the field is lower at both joints than at mid-ring by about 100 to 500 G.

Demagnetization was determined to be a significant factor affecting homogeneity. During testing of the above-described Halbach array, dips in the magnetic field were observed at the magnet joints equivalent to 0.5 mm air gaps. However, the manufacturer of the sample magnet had ground surfaces flat to 0.025 mm (0.001 inches) corresponding to air gaps of only 0.050 mm (0.002 inches) between two magnets. As expected, modeling of 0.050 mm (0.002 inch) air gaps produces inhomogeneities an order of magnitude smaller than those actually observed at the joints. Accordingly, it was determined that there must be some other source of demagnetization other than air gaps between the magnets. It is believed that the grinding process used by the manufacturer was responsible for this difference in demagnetization. Because rare earth magnets and air both have a relative magnetic permeability of about 1, demagnetization due to improper surface grinding to 0.025 mm (0.001 inches) may be modeled as a 0.50 mm (0.002 inch) air gap.

Figure 15:
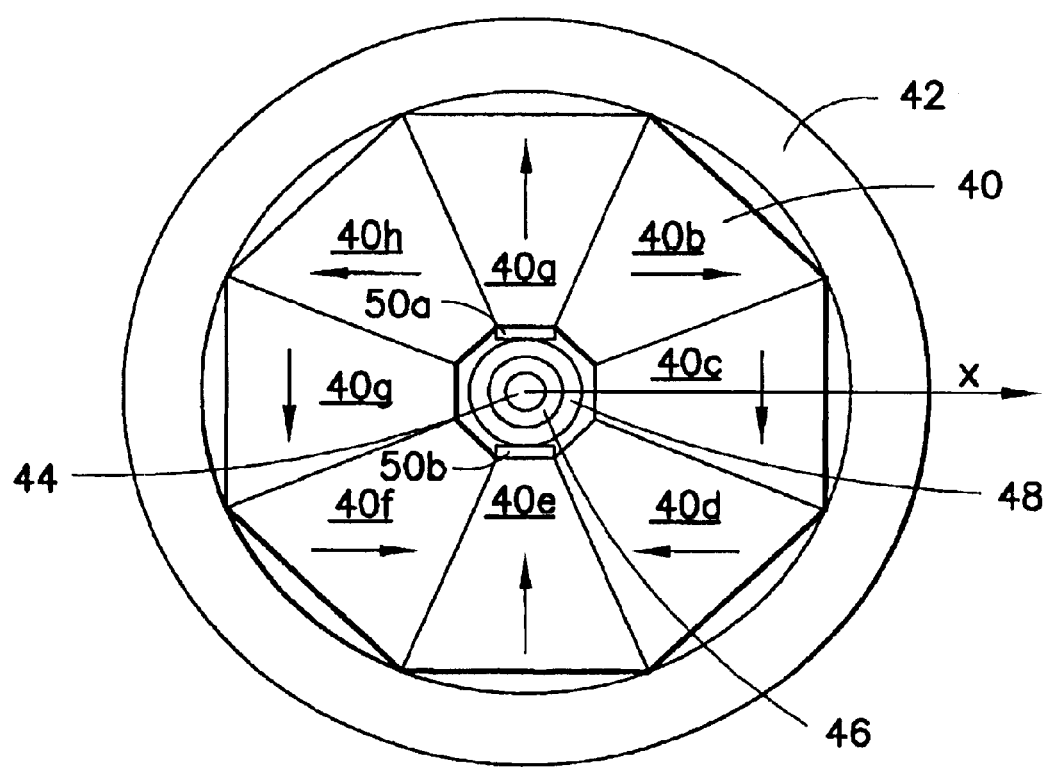
FIG. 15 is a cross-sectional depiction of the Halbach array wherein high magnetic permeability steel straps were placed in the interior surface of two magnet segments as indicated to homogenize the static field.
Figure 16A:
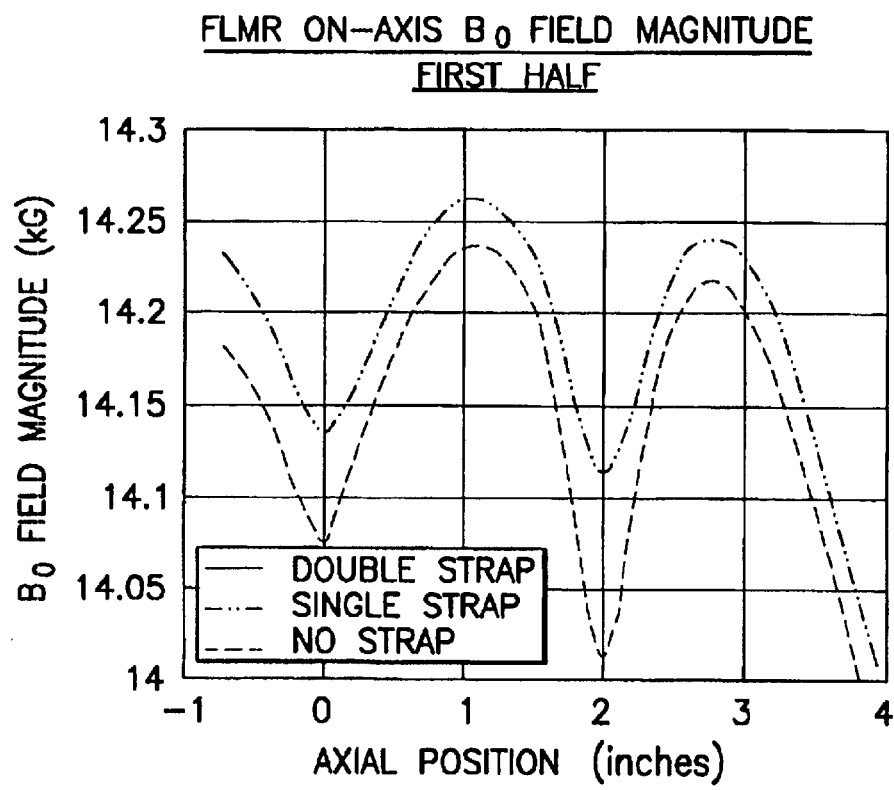
FIGS. 16(a)–(b) are graphical representations of the comparison of the effect of high permeability cobalt-steel straps as pole faces to mitigate static field inhomogeneities at the joints of the Halbach array.

To improve the homogeneity, high-permeability steel straps 50a, 50b ($\mu \approx 6800$ at 1.4 T) were inserted as pole faces as shown in FIG. 15. In the limit of infinite permeability, the surfaces of these pole faces force the field lines to be perpendicular to the straps 50a, 50b. The straps 50a, 50b may be made of 50% cobalt-steel (VACOFLUX 50, VAC Corp., Oklahoma City, Okla.). For the present example, the straps were 0.02 cm (0.008 inches) thick, 30.48 cm (12 inches) long and 0.89 cm (0.350 inches) wide. Pole faces comprised of a single strap or a pair of straps 50a, 50b were tested. FIGS. 16(a) and (b) show that a pair of straps 50a, 50b substantially (if not entirely) mitigates the problem, particularly when chipping is minimized. A thicker pole face of steel with a relative permeability greater than 1000 is also effective because a thicker face is less likely to saturate from flux through the ends than the thinner ones. In addition, wider pole faces will further improve the homogeneity in the region of interest.

Accordingly, magnetic field homogeneity can be improved in the axial direction by greater attention during the manufacturing process not to chip the magnet pieces nor to demagnetize them during grinding. Remaining inhomogeneities can be mitigated by the insertion of steel pole faces.

Figure 17:
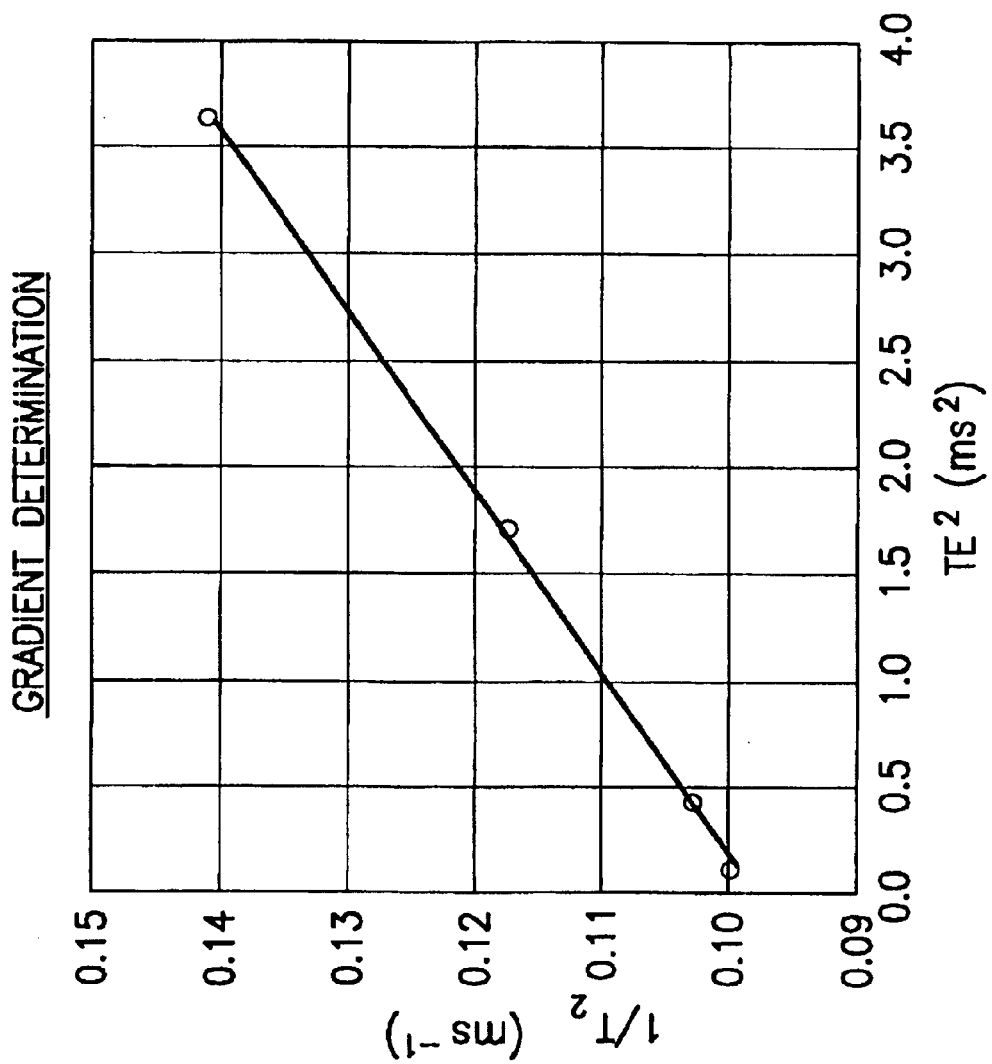
FIG. 17 is a graphical representation of the determination of the static magnetic field gradient at the rf coil.

Determination of Intrinsic $B_0$ Gradient: The intrinsic $B_0$ field gradient may be determined using Equation (9) and a sample whose diffusion constant is known. The echo amplitude decay measured in a CPMG experiment is given by:

$$M(t)=M_0 e^{-t/T_2} e^{-\gamma^2 G^2 TE^2 Dt/12} \qquad (9)$$

where $M_0$ is the equilibrium magnetization, t is the time after the initial rf pulse, G is the gradient, and D is the diffusion constant of the sample. The echo time, $T_E$, is defined as the time between echo peaks or, equivalently, the time between refocusing pulses. Varying the echo time varies the overall decay rate, allowing determination of both $T_2$ and D (as shown in FIG. 17).

G and $T_2$ may be calculated by varying $T_E$ (see FIG. 1). These measurements were performed in a water sample (D=2×10$^{-5}$ cm/s) at two locations in the magnet and yielded results of 99 and 122 G/cm. FIG. 17 shows the relaxation rate as a function of the square of the echo spacing $T_E$. This approach assumes a linear gradient. Though not strictly the case for the prototype magnet, it appears to be a good approximation as the results are in keeping with the anticipated level of inhomogeneity in the magnet. Both measurements were made using magnets where steel straps had largely eliminated any gradient in the axial direction. Thus, the measured gradient was primarily transverse to the flow line. A gradient of 100 G/cm corresponds to an inhomogeneity across the flow line of about 3800 ppm.

Temperature Effects on the Magnet: The resonant frequency of the sample is directly proportional to the magnet field strength and thus is affected by changes in the temperature of the magnet. At 60 MHz, a one-degree change in temperature results in a resonance shift of about 60 kHz for a NdFeB magnet. With a large intrinsic $B_0$ gradient, such shifts can move the sensitive region in the flow line, perhaps changing the sensitive volume and affecting $M_0$ (as discussed below with respect to Sample Volume and Temperature Effect). In the downhole environment, the borehole temperature may differ significantly from the temperature of the fluids being extracted from the formation and flowing through the flow line. A temperature gradient would be created radially across the magnet, affecting the $B_0$ field strength and the Larmor frequency. Consequently, monitoring the temperature at both the outer and inner surface of the magnet may be advisable. Static field strength can also be tracked with a Hall effect probe. Because one need only monitor changes in field strength, the probe may be placed anywhere in the field that is convenient. Field stabilization and tuning will be simpler than in the CMR (Schlumberger's Combinable Magnetic Resonance tool), however, because there will be no buildup of iron fillings.

RF Magnetic ($B_1$) Field

Figure 18:
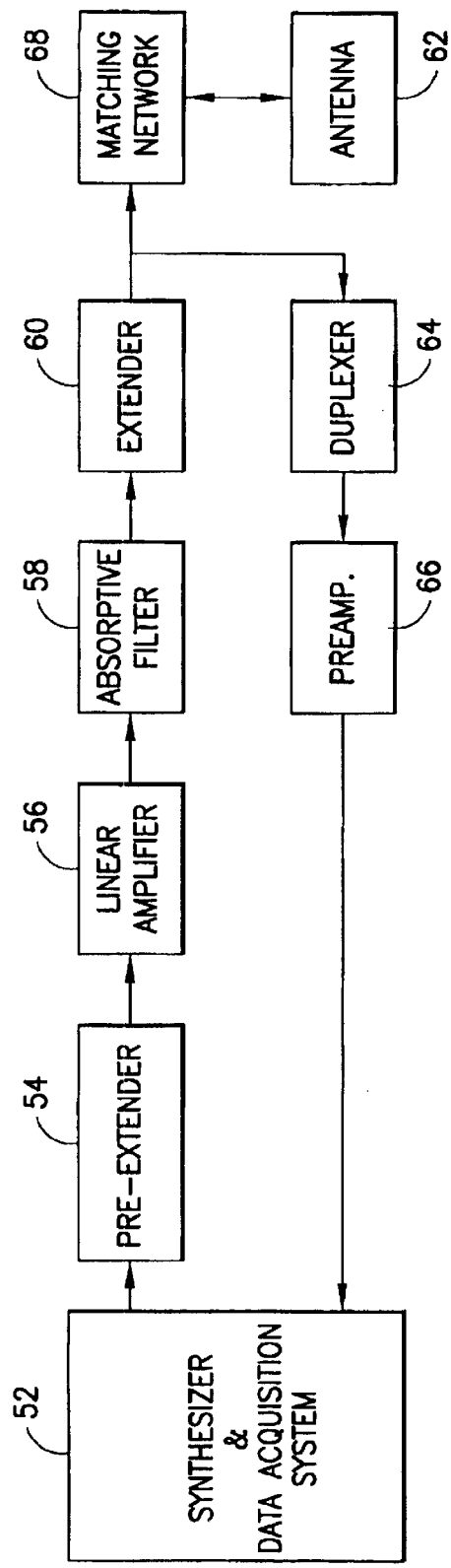
FIG. 18 is a block diagram of the components of the rf system.

Electronics Design Overview: There are two sets of exemplary rf hardware that have been developed for this measurement, a 50 W system, and 1 kW system. Each system is comprised of the components shown in FIG. 18. Synthesizer/digitizer 52 synthesizes the rf pulses for generating the $B_1$ field and acquires and digitizes the spin echo signals for both systems. The rest of the system can be broken down into three components: the transmit chain, the receive chain, and the antenna; each are described below.

The transmit chain is preferably comprised of a pre-extender 54, a linear amplifier 56, an absorptive filter 58, and an extender 60. The extender 60 and pre-extender 54 are circuits which are designed to prevent the noise floor of the synthesizer/digitizer 52 and the linear amplifier 56 from corrupting the noise performance of the receive chain, and to present a high impedance to the antenna 62, thereby making the receive chain the dominant load for the antenna 62 when the transmit chain is not active, such as when the receiver chain is active listening for spin echoes. The absorptive filter 58 is designed to provide a 50Ω load to the linear amplifier 56 (i.e., absorb all power) at all frequencies, and pass only the frequencies of interest to the output port. This is done to ensure amplifier stability in the system stop-band, to reduce low frequency transient effects caused by AC coupling circuits in the linear amplifier 56, and in the case of the 50 W system, to restrict the noise bandwidth of the linear amplifier 56.

The receive chain is preferably comprised of a duplexer 64 and a low-noise preamplifier 66. The function of the duplexer 64 is to present a high impedance to the antenna 62 (i.e., makes the antenna 62 the dominant load for the linear amplifier 56), to provide fast overload recovery, and to protect the preamplifier 66 from damage from the high power pulses driving the antenna 62 while the transmit chain is active.

The antenna 62 may be comprised of a 5-turn coil wound with 18-gauge magnet wire with an inner diameter of about 0.95 cm (⅜-inch). The coil may be embedded in an electrically insulating material and placed inside a non-magnetic metal tube flow line capable of withstanding downhole environments. A winding pitch of 2:1 produced a 1.27 cm (0.5-inch) coil with an inductance of 0.2 μH. To facilitate tuning and matching while the coil is in the magnet, the coil is connected to a 25.4 cm (10-inch) section of 50Ω non-magnetic semi-rigid coaxial cable, which in turn is connected to an external tuning and matching network 68 to transform the impedance of the antenna 62 to 50Ω real. The entire system previously described functions to maintain a 50Ω interface (maximum power transfer) at all times at the juncture of the extender 60, duplexer 64 and antenna matching network 68.

Figure 19:
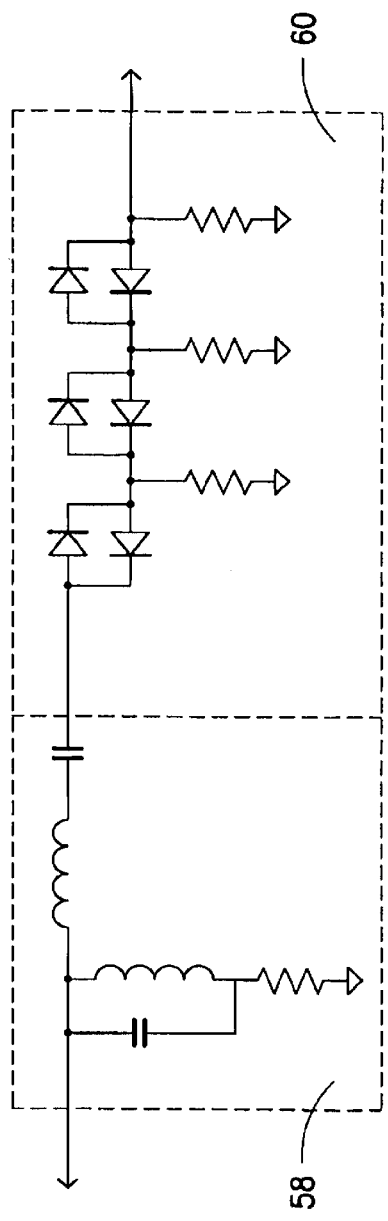
FIG. 19 is a schematic of the absorptive filter and extender for the 50 W system.

The 50 W System: FIG. 19 is a schematic of an embodiment of the absorptive filter 58 and extender 60 for the 50 W system. The filter 58 is comprised of a single pole bandpass filter and a single pole bandstop filter connected in parallel at the input. The output of the bandpass carries the desired signal and the output of the bandstop terminates the undesired signal in a 50Ω termination. The extender 60 is comprised of three cascaded sections of back-to-back PIN diodes. When the transmit signal is present, the amplitude of the signal is sufficient to cause the diodes to conduct effectively connecting the power amplifier 56 to the antenna 62. When the transmit signal is not active, the diodes do not conduct and the amplifier 56 is effectively disconnected from the antenna 62; however, the diode's junction capacitance creates a high pass network with the load impedance and therefore a finite attenuation limit exists. For this reason, the PIN diode is preferred because the intrinsic region of the diode junction acts to widen the depletion region and, therefore, lower the junction capacitance. Surface mounted diodes on a 50Ω stripline structure were used in this design. The extender 60 provides 75 dB of isolation at 60 MHz. To understand why the extender 60 is preferred, consider the following: in a pre-detection bandwidth of 250 kHz, the receiver noise floor due to the thermal noise is −113 dBm referred to the input of the preamplifier 66. If the linear power amplifier 56 has 100 dB of dynamic range (a conservative estimate) then its noise floor is −53 dBm Therefore, at least 60 dB of isolation is required to keep the noise floor of the power amplifier 56 from corrupting the thermal noise floor of the receiver. The pre-extender 54 is a single stage of back-to-back PIN diodes, which prevents the noise floor of the synthesizer/digitizer 52 from being amplified to a level which can leak through the extender 60.

Receiver: The preamplifier 66 includes a built-in duplexer 64, which is specified to protect the input from up to 1 kW for 5 μsec at a 5% duty cycle. One skilled in the art would recognize that other duplexers may be suitably employed. The preamplifier uses a quarter-wave section of transmission line to transform the low impedance of the duplexer 64 during the transmit phase to a very high impedance, relative to the antenna 62, preferably two or more orders of magnitude greater. This preamplifier 66 is used in both the 50 W and 1 kW systems.

Figure 20:
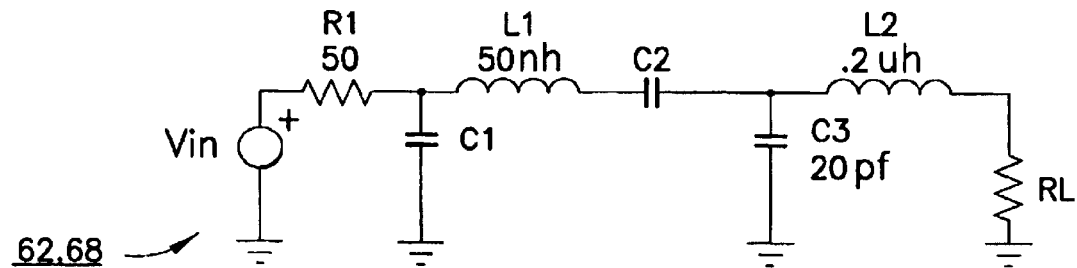
FIG. 20 is a schematic of an equivalent circuit to the rf coil (L2) and the matching network, wherein the if coil is physically removed from the tuning and matching elements.

Antenna: FIG. 20 shows an embodiment of the equivalent circuit of the antenna 62 and the matching network 68. Due to the physical constraints of the system, the antenna 62 should be physically removed from the tuning and matching elements 68. However, the interconnecting coaxial cable capacitance caused a parallel resonance to occur very close to the desired frequency of operation (60 MHz) and the real part of the impedance at resonance was very high (the unloaded Q times the reactance of the coil or roughly 8 kΩ). To use this resonance would have required a transformation ratio of approximately 160:1 in the matching network 68, which would have resulted in a very narrow band match and very sensitive and unstable adjustments. Therefore, it was decided to make use of the series resonance which required a more moderate transformation of about 60:1. This resulted in an impedance match of broader bandwidth match and, therefore, more easily adjusted. C3 in FIG. 20 is the cable capacitance and C2 (which tunes the circuit) is an adjustable capacitor which series resonates the equivalent inductance of the parallel combination of L2 and C3. C1 and L1 form an "L" matching network. C1 is also adjustable and controls the transformation ratio or loading. The value of L1 also changes as a function of transformation ratio but its effective value can be, and is, altered using C2 at the expense of some interaction between the two adjustments. This interaction has not proved to be a problem in practice, however. Vin and R1 represent the generator/load.

1 kW System: Most of the hardware for the 1 kW system remains the same at the 50 W system The exceptions are the power amplifier 56, the absorptive filter 58, and the extender 60.

In one embodiment, the amplifier 56 can deliver 1 kW peak pulses and has a bandwidth of 10–130 MHz. One skilled in the art would recognize that other amplifiers may be suitably employed.

Figure 21:
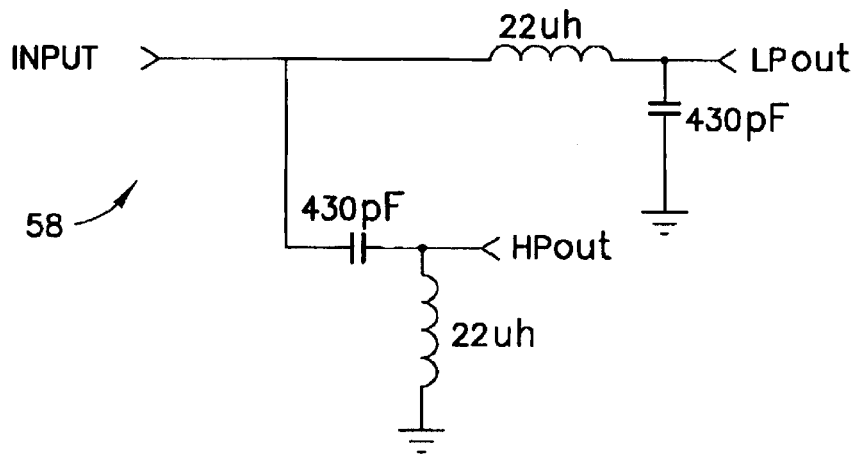
FIG. 21 is a schematic of the absorptive filter for the 1 kW system, wherein the filter accommodates the carbon, sodium, and hydrogen resonances (~15–60 MHz) as well as increased power handling capability.

FIG. 21 is a schematic diagram of an embodiment of the absorptive filter 58 for the 1 kW system. This filter 58 was designed to accommodate the 60 MHz hydrogen resonance and the 15 MHz sodium and carbon resonances as well as increased power handling capability. This was accomplished by using high pass and low pass filter sections each with two poles and cutoffs at 5 MHz. The input impedance remains within 1.5 Ω of 50Ω from DC to greater than 100 MHz.

Figure 22:
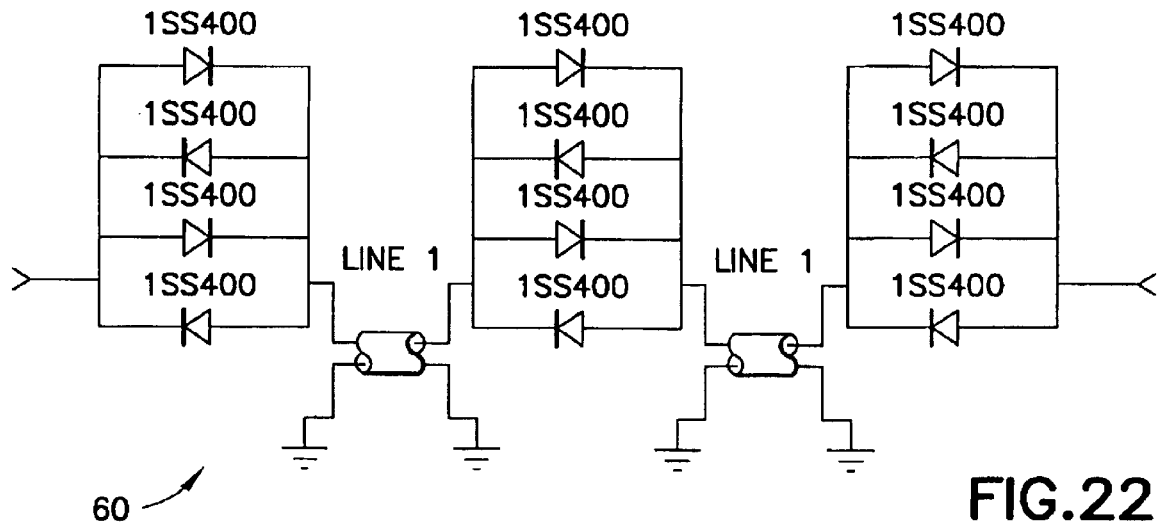
FIG. 22 is a schematic for the 1 kW system extender wherein a quarter-wave transmission line is inserted between each section of diodes to improve the extender's isolation.

FIG. 22 is a schematic diagram of an embodiment of the 1 kW extender 60. In order to handle the peak currents involved in the 1 kW system, diodes with higher current handling capability should be preferably used. High-speed switching diodes were selected for this embodiment to provide peak surge current capability of 5 A per diode for a 1 ms pulse. One skilled in the art would recognize that other diodes may be suitably employed. The price for increased handling capability is a higher junction capacitance of 0.7 pF as opposed to 0.2 pF with the PIN diodes. This reduced the isolation possible per stage. To increase the isolation of each stage a quarter-wave transmission line section at 60 MHz was used between each section. This transformed the high impedance of nonconducting (isolating) diodes to a low impedance (low voltage) at the next diode stage. The features just mentioned resulted in an extender 60 which provides 75 dB of isolation at 60 MHz and also at 15 MHz since the high pass behavior of the diode capacitance against the load resistance compensates the reduced isolation resulting from the shortened transmission line at 15 MHz. Because the peak pulse power is increased by 13 dB over the 50 W system, the isolation necessary also is increased by that amount. This would necessitate the use of blanking the power amplifier 56.

Determination of $B_1$ Field Strength: The strength of the $B_1$ field of these embodiments was determined in two ways. First, a small pickup coil was placed inside the rf coil. The pickup coil is comprised of a 3-mm diameter loop of thin semirigid coaxial cable with its outer conductor slightly stripped back to expose the inner conductor in series with a 50Ω resistor. The resistor was included to match the input impedance of the oscilloscope used to observe the induced signal. The measurement was made inside the magnet. The oscillating $B_1$ field induces an electromagnetic field in the coil given by $$\varepsilon = -N\frac{d\phi}{dt} \qquad (10)$$
$$= -NA\frac{dB}{dt}$$

where the number of turns, N, equals 1, and the area, A, equals 7 mm².

With an rf amplifier, output power of 39 W, the $B_1$ field in the laboratory frame was calculated to be 20 G.

The second determination was made directly with NMR. An initial rf pulse was applied to the system, followed by a second pulse to produce an echo. The peak echo amplitude was monitored as the initial pulse length was varied in an effort to maximize the peak echo amplitude. When this occurred, it was assumed that the first pulse mutated the magnetization by 90 degrees. The refocusing pulse was essentially kept constant, though it was modified iteratively as the first pulse was moving toward 90 degrees. A problem with this method is that the echo peak is the integration of the signal from all excited frequencies. In an inhomogeneous $B_0$ field, all isochromats are nutated differently, thus obscuring the meaning of a "90 degree pulse." More significantly, the maximum peak amplitude may occur when the on-resonance spins experience something other than a 90 degree pulse. This problem can be overcome by maximizing only the on-resonance signal magnitude. To obtain this signal, one may Fourier transform the complex time domain data and keep only that component that has no frequency offset. Accordingly, the maximum time domain signal occurred with an initial pulse of 5.5 µs. The governing equations are $$\theta = \gamma B_{1,rot}\tau \qquad (11)$$
$$= \gamma B_{1,lab}\frac{\tau}{2}$$

where θ is the flip angle, γ is the gyromagnetic ratio, and τ is the pulse length. Therefore, $B_{1,lab}$ is 21.4 G at 60 MHz and 39 W, and the two methods are in agreement.

Optimization of 90 degree and 180 degree Pulses: Rf pulses were adjusted to maximize the magnitude of the signal at the peak of the first echo. This is equivalent to integrating the signal over all frequencies. Once echoes were detected, optimization proceeded by selecting a fixed duration for the second (refocusing) pulse while varying the initial pulse. This was taken as the 90 degree pulse duration and the duration of the refocusing pulse was set to twice as long as the 90 degree pulse. On the 50 W system, with a measured rf amplifier power output of 39 W, the pulses were 5.5 and 11.0 µs, respectively, for $^1$H.

An alternative approach was to perform a two-dimensional experiment where all combinations of initial and refocusing pulse durations within prescribed ranges were tested. In that experiment a maximum signal was observed with pulses of 4.8 and 7.2 µs, respectively. It should be noted that the maximum was relatively broad so that a number of combinations worked almost equally well. The 1:2 pulse ratio was not used because measurements were made in an inhomogeneous static field so that the rf pulses are slice selective, exciting only a portion of the sample. Short pulses will excite or refocus a larger number of spins than longer pulses, but with lower efficiency. This method is disclosed in "Spin Dynamics of Carr-Purcell-Meiboom-Gill-like Sequences in Grossly Inhomogeneous $B_0$ and $B_1$ Fields and Application to NMR Well Logging," *Journal of Magnetic Resonance* 143, 120–135 (2000) by Martin D. Hurlimann et al. and "Optimization of Timing in Carr-Purcell-Meiboom-Gill Sequences," *Magnetic Resonance Imaging*, 19, 375–378 (2001) by Martin D. Hurlimann, incorporated by reference herein in their entireties.

Figure 16B:
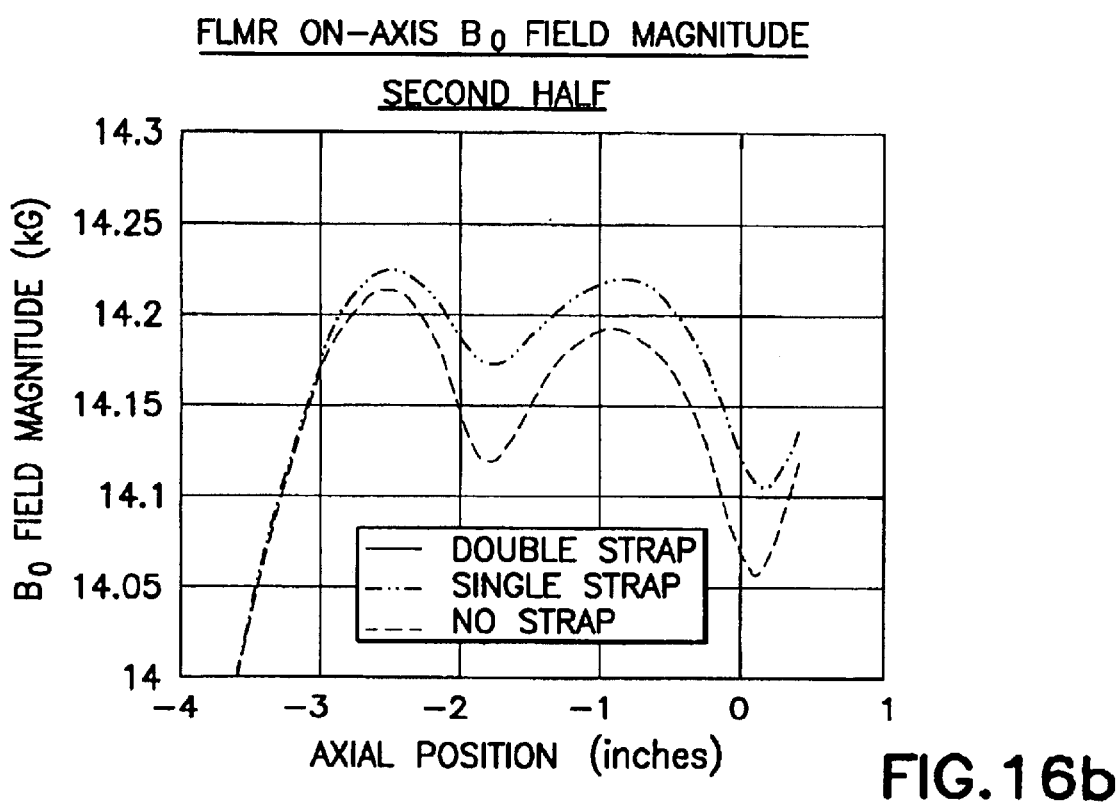

Sample Volume and Temperature Effect: In the laboratory, the temperature effect on sample was explored using the rf coil described above (0.95 cm (0.375 inches) in length and wound on a plastic tube (the flow line) that has an outer diameter of 1.27 cm (0.5 inches)) was used. The inner diameter of the tube (flow line) is 0.64 cm (0.25 inches). In a simplistic approach, one can ignore end effects of the solenoid and assume a perfectly homogeneous $B_1$ field over a length of 1 cm. Thus, if the entire volume in that region of the tube is excited, the sample volume is approximately 0.32 ml. In the presence of a $B_0$ gradient, however, the rf pulses become slice selective and the volume is reduced. The measured gradient at the location of the coil (−3.81 cm (−1.5 inches) from the magnet center, as shown in FIGS. 16(*a*) and (*b*)) is on the order of 100 G/cm. Time-of-flight measurements (as discussed above) indicate that the gradient in the flow (axial) direction is about 50 G/cm. Therefore, the gradient makes an angle of 60 degrees with the magnet axis, and the excited volume is oriented at a 30 degree angle with respect to the axis. The thickness of the slice refocused by the 180 degree pulse can be obtained by recognizing that where $$\gamma(\sqrt{(\Delta B_0)^2 + B_1^2})t_{180}=2\pi \qquad (12)$$

the magnetization is returned to its original orientation. Applying this, the full width of the central lobe is $$\Delta f_{FW} = \frac{\sqrt{3}}{t_{180}} \qquad (13)$$

With $t_{180}$ equal to 11 µs and a gradient of 100 G/cm, the slice thickness is about 0.4 cm. If this elliptical slice, oriented at about 30 degrees with respect to the flow line, is assumed to be centered on the coil, then the excited volume is about 0.25 ml. At a higher power, the 1.8 µs refocusing pulses excite a 2.3-cm thick slice, thus exciting the entire cross section of the tube.

Figure 23:
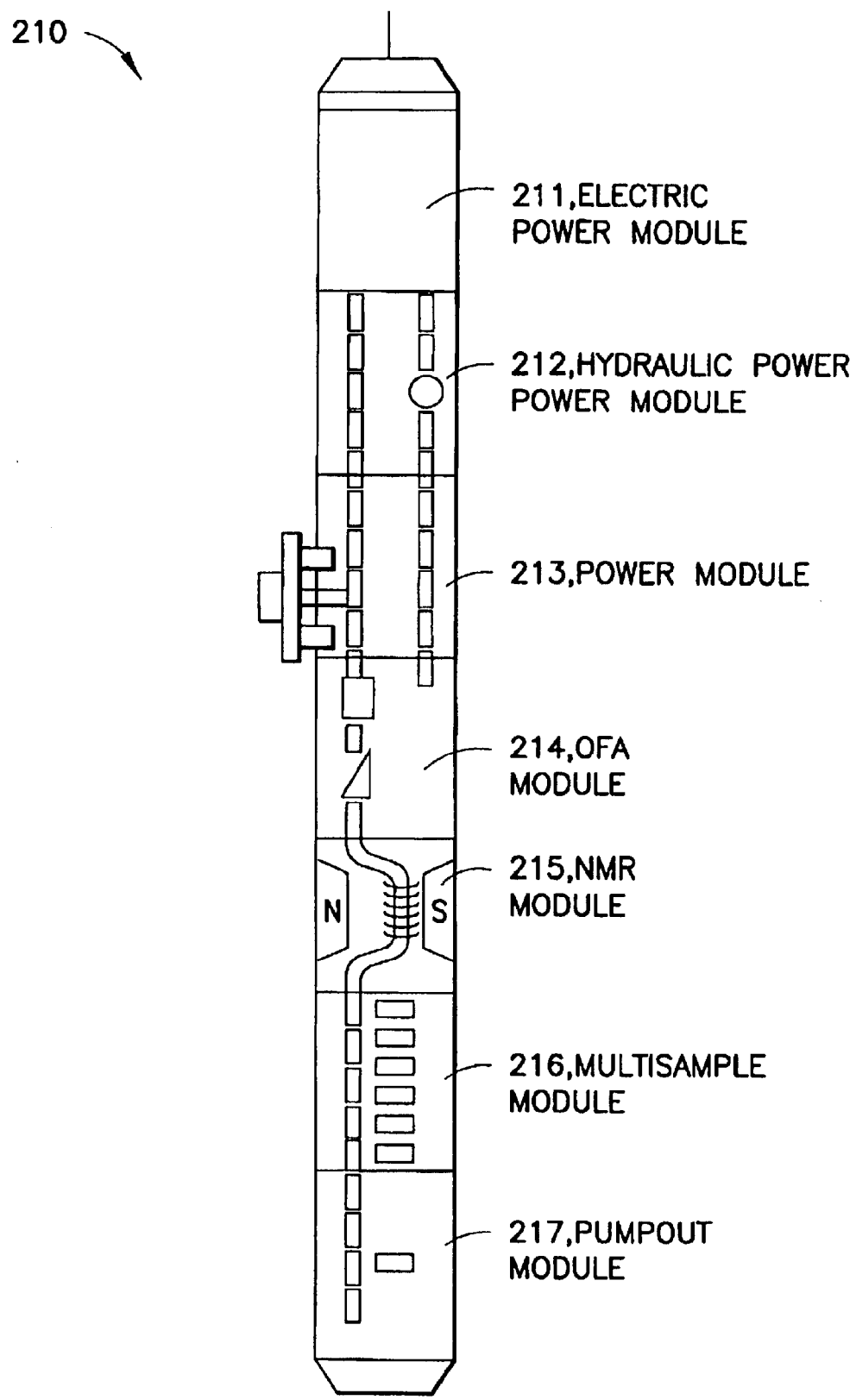
FIG. 23 illustrates a schematic diagram of a fluid sampling tool utilized in extracting formation fluid in accordance with the present invention.

The foregoing description of the preferred and alternate embodiments may be incorporated into a formation testing apparatus 210 such as the one described in FIG. 23 (and described in commonly owned U.S. Pat. No. 6,346,813 to Kleinberg which is incorporated by reference in its entirety herein). The tool 210 has an electric power module 211 and an hydraulic power module 212 as known in the art. The probe module 213 is deployed so as to make a hydraulic seal with the formation. The pumpout module 217 lowers the pressure in the flow line in a controlled manner so as to extract fluid from the formation while maintaining the pressure near the original formation pressure. Samples may be optionally monitored by an optical fluid analyzer 214 and may be retained for transport to surface laboratories in the multisample module 216. The NMR module which is the subject of the present invention is shown as element 215.

The foregoing description of the preferred and alternate embodiments of the present invention has been presented for purposes of illustration and description. It is not intended to be exhaustive or limit the invention to the precise form disclosed. Obviously, many modifications and variations will be apparent to those skilled in the art. The embodiments were chosen and described in order to best explain the principles of the invention and its practical application thereby enabling others skilled in the art to understand the invention for various embodiments and with various modifications as are suited to the particular use contemplated. It is intended that the scope of the invention be defined by the accompanying claims and their equivalents.

We claim:

1. A method of making a nuclear magnetic resonance measurement on a flowing fluid comprising:
    a) flowing the fluid through a static magnetic field;
    b) applying a group of oscillating magnetic field pulses to the flowing fluid, wherein each group of pulses is comprised of an initial pulse and one or more refocusing pulses, and wherein the group of pulses further comprise a spoiler rf pulse;
    c) detecting magnetic resonance signals from the flowing fluid;
    d) after a wait time, repeating (b) and (c) one or more times, wherein at least two of the repetitions have varied wait times; and
    e) analyzing the detected magnetic resonance signals to extract information about the flowing fluid.

2. The method of claim 1, wherein the detected magnetic resonance signals are corrected for spin dynamic effects.

3. The method of claim 1, wherein detecting magnetic resonance signals comprises detecting magnetic resonance spin echoes after each refocusing pulse.

4. The method of claim 3, wherein analyzing the detected magnetic resonance signals comprises analyzing the first spin echo from each group of pulses.

5. The method of claim 1, wherein each repetition has a progressively longer wait time.

6. The method of claim 1, wherein the fluid is extracted from an earth formation.

7. The method of claim 1, wherein analyzing the detected magnetic resonance signals includes determining initial polarization buildup.

8. The method of claim 1, wherein the static magnetic field includes a magnetic field gradient and wherein analyzing the detected magnetic resonance signals includes measuring the flow rate of the flowing fluid.

9. The method of claim 8, wherein measuring the flow rate includes monitoring the magnetic resonance signals for a change in frequency between wait times.

10. The method of claim 8, further comprising comparing the amplitude of an early detected echo to one or more subsequent echoes to determine the onset of turbulence in the flowing fluid.

11. The method of claim 10, wherein the first echo is compared to one or more later echoes.

12. The method of claim 8, further comprising comparing the amplitude of the free induction decay following the initial pulse to one or more subsequent echoes to determine the onset of turbulence.

13. The method of claim 8, wherein detecting magnetic resonance signals comprises separately detecting magnetic resonance spin echoes after each refocusing pulse; and wherein measuring the flow rate comprises analyzing odd and even echoes to determine flow rate.

14. The method of claim 13, wherein analyzing the odd and even echoes includes analyzing the phase of the odd and even echoes.

15. The method of claim 13, wherein analyzing the odd and even echoes includes analyzing the amplitude of the odd and even echoes.

16. The method of claim 13, further comprising detecting the onset of turbulence in the flowing fluid.

17. The method of claim 16, wherein detecting the onset of turbulence is comprised of comparing the amplitude of the first detected echo to subsequent echoes.

18. The method of claim 16, wherein detecting the onset of turbulence is comprised of comparing the amplitude of the free induction decay following the initial pulse to subsequent echoes.

19. A method of analyzing a fluid in a downhole environment comprising:
a) introducing a fluid sampling tool into a well bore that traverses an earth formation;
b) using the fluid sampling tool to extract the fluid from the earth formation into a flow channel within the tool;
c) flowing the fluid through a static magnetic field;
d) applying one or more groups of oscillating magnetic field pulses to the fluid in the flow channel, wherein the group of pulses comprises an initial pulse followed by one or more refocusing pulses, wherein at least two groups of pulses are generated after a varied wait time, and wherein the group of pulses further comprise a spoiler rf pulse;
e) detecting from the flowing fluid magnetic resonance signals within each group of pulses; and
f) analyzing the detected signals to extract information about the flowing fluid.

20. The method of claim 19, wherein each repetition has a progressively longer wait time.

21. An apparatus for analyzing a fluid in a downhole environment comprising:
a) means for extracting the fluid from an earth formation into a flow channel within a well logging tool;
b) means for generating a static magnetic field within the flow channel;
c) means for generating one or more groups of oscillating magnetic field pulses to the fluid in the flow channel, wherein each group of pulses is comprised of an initial pulse followed by one or more refocusing pulses, wherein at least two groups of pulses are generated after a varied wait time, and wherein the group of pulses further comprise a spoiler rf pulse;
d) means for detecting magnetic resonance signals; and
e) means for analyzing the detected magnetic resonance signals.

22. The apparatus of claim 21, wherein each repetition has a progressively longer wait time.

23. The apparatus of claim 21, wherein said static magnetic field is generated by a series of magnets comprising an Halbach array.

24. The apparatus of claim 23, wherein one or more steel straps are inserted as one or more pole faces of the Halbach array.

25. The apparatus of claim 21, further comprising means to monitor the onset of turbulence of the fluid in the flow channel.

26. The apparatus of claim 25, further comprising means to separately detect magnetic resonance signals of even oscillating pulses and odd oscillating pulses.

27. The apparatus of claim 21, wherein the static magnetic field includes a magnetic field gradient and further including means to determine the flow rate of the fluid in the flow channel.

28. A method of making a nuclear magnetic resonance measurement on a flowing fluid comprising:
a) flowing the fluid through a static magnetic field, wherein the static magnetic field includes a magnetic field gradient;
b) applying a group of oscillating magnetic field pulses to the flowing fluid, wherein each group of pulses is comprised of an initial pulse and one or more refocusing pulses;
c) detecting magnetic resonance signals from the flowing fluid;
d) after a wait time, repeating (b) and (c) one or more times, wherein at least two of the repetitions have varied wait times; and
e) analyzing the detected magnetic resonance signals to measure the flow rate of the flowing fluid by monitoring the magnetic resonance signals for a change in frequency between wait times.

* * * * *